US008761880B2

(12) United States Patent  
Maskara et al.

(10) Patent No.: US 8,761,880 B2
(45) Date of Patent: Jun. 24, 2014

(54) HIS CAPTURE VERIFICATION USING ELECTRO-MECHANICAL DELAY

(75) Inventors: Barun Maskara, Blaine, MN (US); Jiang Ding, Shoreview, MN (US); Shantha Arcot-Krishnamurthy, Vadnais Heights, MN (US); Allan C. Shuros, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 83 days.

(21) Appl. No.: 13/404,814

(22) Filed: Feb. 24, 2012

(65) Prior Publication Data

US 2012/0239106 A1 Sep. 20, 2012

Related U.S. Application Data

(60) Provisional application No. 61/452,412, filed on Mar. 14, 2011.

(51) Int. Cl.
*A61N 1/365* (2006.01)
*A61N 1/362* (2006.01)

(52) U.S. Cl.
CPC ........... *A61N 1/36514* (2013.01); *A61N 1/3627* (2013.01); *A61N 1/365* (2013.01); *A61N 1/36564* (2013.01)
USPC .................................. 607/17; 607/9; 607/28

(58) Field of Classification Search
CPC . A61N 1/3627; A61N 1/365; A61N 1/36564; A61N 1/36514
USPC .................................................. 607/17, 23, 9
See application file for complete search history.

(56) References Cited

U.S. PATENT DOCUMENTS

| | | | |
|---|---|---|---|
| 3,942,536 A | 3/1976 | Mirowski et al. |
| 4,136,703 A | 1/1979 | Wittkampf |
| 4,543,956 A | 10/1985 | Herscovici |
| 4,589,420 A | 5/1986 | Adams et al. |
| 4,603,705 A | 8/1986 | Speicher et al. |
| 4,627,439 A | 12/1986 | Harris |
| 4,630,204 A | 12/1986 | Mortara |
| 4,751,931 A | 6/1988 | Briller et al. |
| 4,799,486 A | 1/1989 | DuFault |

(Continued)

FOREIGN PATENT DOCUMENTS

| | | | |
|---|---|---|---|
| AU | 205319498 B2 | 7/2011 |
| EP | 1234597 A2 | 8/2002 |

(Continued)

OTHER PUBLICATIONS

Arcot-Krishnamurthy, S., et al., "Timing for His-Bundle Pacing", U.S. Appl. No. 13/277,617, filed Oct. 20, 2011, 40 pgs.

(Continued)

*Primary Examiner* — Christopher D Koharski
*Assistant Examiner* — Philip Edwards
(74) *Attorney, Agent, or Firm* — Schwegman, Lundberg & Woessner, P.A.

(57) ABSTRACT

Stimulation energy can be provided to a His-bundle to activate natural cardiac contraction mechanisms. Interval information can be used to describe a cardiac response to His-bundle stimulation, and the interval information can provide cardiac stimulation diagnostic information. For example, interval information can be used to discriminate between intrinsic conduction cardiac contractions and contractions responsive to His-bundle pacing.

20 Claims, 9 Drawing Sheets

(56) References Cited

U.S. PATENT DOCUMENTS

| | | |
|---|---|---|
| 4,799,493 A | 1/1989 | DuFault |
| 4,892,102 A | 1/1990 | Astrinsky |
| 5,083,564 A | 1/1992 | Scherlag |
| 5,267,560 A | 12/1993 | Cohen |
| 5,313,953 A | 5/1994 | Yomtov et al. |
| 5,320,642 A | 6/1994 | Scherlag |
| 5,336,252 A | 8/1994 | Cohen |
| 5,370,665 A | 12/1994 | Hudrlik |
| 5,381,790 A | 1/1995 | Kanesaka |
| 5,433,735 A | 7/1995 | Zanakis et al. |
| 5,456,706 A | 10/1995 | Pless et al. |
| 5,500,008 A | 3/1996 | Fain |
| 5,609,158 A | 3/1997 | Chan |
| 5,628,778 A | 5/1997 | Kruse et al. |
| 5,634,899 A | 6/1997 | Shapland et al. |
| 5,683,447 A | 11/1997 | Bush et al. |
| 5,702,427 A | 12/1997 | Ecker et al. |
| 5,728,140 A | 3/1998 | Salo et al. |
| 5,733,323 A | 3/1998 | Buck et al. |
| 5,755,766 A | 5/1998 | Chastain et al. |
| 5,800,464 A | 9/1998 | Kieval |
| 5,807,306 A | 9/1998 | Shapland et al. |
| 5,810,887 A | 9/1998 | Accorti, Jr. et al. |
| 5,814,079 A | 9/1998 | Kieval |
| 5,851,227 A | 12/1998 | Spehr |
| 5,871,506 A | 2/1999 | Mower |
| 5,876,399 A | 3/1999 | Chia et al. |
| 5,876,431 A | 3/1999 | Spehr et al. |
| 5,908,392 A | 6/1999 | Wilson et al. |
| 5,941,868 A | 8/1999 | Kaplan et al. |
| 5,944,710 A | 8/1999 | Dev et al. |
| 6,006,139 A | 12/1999 | Kruse et al. |
| 6,007,476 A | 12/1999 | Wascher et al. |
| 6,024,739 A | 2/2000 | Ponzi et al. |
| 6,059,726 A | 5/2000 | Lee et al. |
| 6,070,104 A | 5/2000 | Hine et al. |
| 6,086,582 A | 7/2000 | Altman et al. |
| 6,123,084 A | 9/2000 | Jandak et al. |
| 6,165,164 A | 12/2000 | Hill et al. |
| 6,212,434 B1 | 4/2001 | Scheiner et al. |
| 6,236,887 B1 | 5/2001 | Ben-Haim et al. |
| 6,254,573 B1 | 7/2001 | Haim et al. |
| 6,256,541 B1 | 7/2001 | Heil et al. |
| 6,267,778 B1 | 7/2001 | Cohen |
| 6,285,909 B1 | 9/2001 | Sweeney et al. |
| 6,309,370 B1 | 10/2001 | Haim et al. |
| 6,341,235 B1 | 1/2002 | Mower |
| 6,345,204 B1 | 2/2002 | Scheiner et al. |
| 6,358,247 B1 | 3/2002 | Altman et al. |
| 6,363,286 B1 | 3/2002 | Zhu et al. |
| 6,416,510 B1 | 7/2002 | Altman et al. |
| 6,430,441 B1 | 8/2002 | Levine |
| 6,463,334 B1 | 10/2002 | Flynn et al. |
| 6,468,263 B1 | 10/2002 | Fischell et al. |
| 6,484,057 B2 | 11/2002 | Ideker et al. |
| 6,526,314 B1 | 2/2003 | Eberle et al. |
| 6,535,766 B1 | 3/2003 | Thompson et al. |
| 6,540,725 B1 | 4/2003 | Ponzi |
| 6,544,270 B1 | 4/2003 | Zhang |
| 6,547,787 B1 | 4/2003 | Altman et al. |
| 6,556,874 B2 | 4/2003 | Audoglio |
| 6,560,489 B2 | 5/2003 | Hauck |
| 6,575,931 B1 | 6/2003 | Ponzi |
| 6,585,716 B2 | 7/2003 | Altman |
| 6,606,517 B1 | 8/2003 | Park et al. |
| 6,609,027 B2 | 8/2003 | Kroll et al. |
| 6,623,473 B1 | 9/2003 | Ponzi |
| 6,623,474 B1 | 9/2003 | Ponzi |
| 6,650,940 B1 | 11/2003 | Zhu et al. |
| 6,702,744 B2 | 3/2004 | Mandrusov et al. |
| 6,702,777 B2 | 3/2004 | Haim et al. |
| 6,718,206 B2 | 4/2004 | Casavant |
| 6,768,923 B2 | 7/2004 | Ding et al. |
| 6,775,571 B1 | 8/2004 | Kroll |
| 6,801,807 B2 | 10/2004 | Abrahamson |
| 6,810,286 B2 | 10/2004 | Donovan et al. |
| 6,823,210 B2 | 11/2004 | Eberle et al. |
| 6,855,124 B1 | 2/2005 | Gonzalez et al. |
| 6,905,476 B2 | 6/2005 | Ponzi |
| 6,909,920 B2 | 6/2005 | Lokhoff et al. |
| 6,931,286 B2 | 8/2005 | Sigg et al. |
| 6,937,897 B2 | 8/2005 | Min et al. |
| 7,027,866 B2 * | 4/2006 | Warkentin ............... 607/23 |
| 7,027,876 B2 | 4/2006 | Casavant et al. |
| 7,096,051 B1 | 8/2006 | Alder |
| 7,127,300 B2 | 10/2006 | Mazar et al. |
| 7,187,970 B2 | 3/2007 | Shemer et al. |
| 7,245,973 B2 | 7/2007 | Liu et al. |
| 7,280,872 B1 | 10/2007 | Mosesov et al. |
| 7,317,950 B2 | 1/2008 | Lee |
| 7,319,900 B2 | 1/2008 | Kim et al. |
| 7,330,750 B2 | 2/2008 | Erkkila et al. |
| 7,359,837 B2 | 4/2008 | Drew |
| 7,395,042 B2 | 7/2008 | Alder |
| 7,395,117 B2 | 7/2008 | Mazar et al. |
| 7,400,931 B2 | 7/2008 | Mandrusov et al. |
| 7,421,292 B1 | 9/2008 | Kroll |
| 7,447,544 B1 | 11/2008 | Kroll |
| 7,457,664 B2 * | 11/2008 | Zhang et al. ............. 607/9 |
| 7,460,914 B2 | 12/2008 | Mandrusov et al. |
| 7,509,170 B2 | 3/2009 | Zhang et al. |
| 7,512,440 B2 | 3/2009 | Ortega et al. |
| 7,529,584 B2 | 5/2009 | Laske et al. |
| 7,792,580 B2 | 9/2010 | Borowitz et al. |
| 7,817,784 B2 | 10/2010 | Wang et al. |
| 8,005,544 B2 | 8/2011 | Zhu et al. |
| 8,010,191 B2 | 8/2011 | Zhu et al. |
| 8,010,192 B2 | 8/2011 | Zhu et al. |
| 8,014,861 B2 | 9/2011 | Zhu et al. |
| 8,050,756 B2 | 11/2011 | Zhu et al. |
| 8,078,287 B2 | 12/2011 | Liu et al. |
| 8,346,358 B2 | 1/2013 | Ortega et al. |
| 8,423,139 B2 | 4/2013 | Zhu et al. |
| 8,428,715 B2 | 4/2013 | Ortega et al. |
| 8,437,848 B2 | 5/2013 | Ortega et al. |
| 8,538,521 B2 | 9/2013 | Zhu et al. |
| 8,543,203 B2 | 9/2013 | Zhu et al. |
| 8,565,880 B2 | 10/2013 | Dong et al. |
| 2001/0031986 A1 | 10/2001 | Hauck |
| 2001/0044619 A1 | 11/2001 | Altman |
| 2002/0010492 A1 | 1/2002 | Donovan et al. |
| 2002/0016615 A1 | 2/2002 | Dev et al. |
| 2002/0022863 A1 | 2/2002 | Hauck |
| 2002/0026228 A1 | 2/2002 | Schauerte |
| 2002/0058981 A1 | 5/2002 | Zhu et al. |
| 2002/0099413 A1 | 7/2002 | Mower |
| 2002/0120318 A1 | 8/2002 | Kroll et al. |
| 2002/0183720 A1 | 12/2002 | Hill et al. |
| 2002/0193836 A1 | 12/2002 | Schmidt |
| 2003/0032938 A1 | 2/2003 | Altman |
| 2003/0078625 A1 | 4/2003 | Casavant |
| 2003/0083711 A1 | 5/2003 | Yonce et al. |
| 2003/0093104 A1 | 5/2003 | Bonner et al. |
| 2003/0105492 A1 | 6/2003 | Ding et al. |
| 2003/0105496 A1 | 6/2003 | Yu et al. |
| 2003/0109914 A1 | 6/2003 | Westlund et al. |
| 2003/0113303 A1 | 6/2003 | Schwartz |
| 2003/0125615 A1 | 7/2003 | Schwartz |
| 2003/0129750 A1 | 7/2003 | Schwartz |
| 2003/0171723 A1 | 9/2003 | Ponzi |
| 2003/0195470 A1 | 10/2003 | Ponzi |
| 2004/0064176 A1 | 4/2004 | Min et al. |
| 2004/0104782 A1 | 6/2004 | Ruffieux |
| 2004/0106958 A1 | 6/2004 | Mathis et al. |
| 2004/0122484 A1 | 6/2004 | Hatlestad et al. |
| 2004/0186546 A1 | 9/2004 | Mandrusov et al. |
| 2004/0213770 A1 | 10/2004 | Seward et al. |
| 2004/0214182 A1 | 10/2004 | Sharma et al. |
| 2004/0215251 A1 | 10/2004 | Sharma et al. |
| 2004/0260374 A1 | 12/2004 | Zhang et al. |
| 2005/0136385 A1 | 6/2005 | Mann et al. |
| 2005/0137671 A1 | 6/2005 | Liu et al. |
| 2005/0277993 A1 | 12/2005 | Mower |
| 2006/0030810 A1 | 2/2006 | Mandrusov et al. |

(56) References Cited

U.S. PATENT DOCUMENTS

| | | | |
|---|---|---|---|
| 2006/0064027 A1 | 3/2006 | Borowitz et al. | |
| 2006/0094970 A1 | 5/2006 | Drew | |
| 2006/0094971 A1 | 5/2006 | Drew | |
| 2006/0094972 A1 | 5/2006 | Drew | |
| 2006/0095092 A1 | 5/2006 | Drew | |
| 2006/0104596 A1 | 5/2006 | Askins et al. | |
| 2006/0142812 A1 | 6/2006 | Ortega et al. | |
| 2006/0224197 A1 | 10/2006 | Havel et al. | |
| 2006/0235489 A1 | 10/2006 | Drew et al. | |
| 2006/0287691 A1 | 12/2006 | Drew | |
| 2007/0027488 A1 | 2/2007 | Kaiser et al. | |
| 2007/0032733 A1 | 2/2007 | Burton | |
| 2007/0093872 A1 | 4/2007 | Chirife et al. | |
| 2007/0093874 A1 | 4/2007 | Chirife et al. | |
| 2007/0233216 A1 | 10/2007 | Liu et al. | |
| 2007/0239219 A1 | 10/2007 | Salo et al. | |
| 2007/0244402 A1 | 10/2007 | Brockway et al. | |
| 2007/0255147 A1 | 11/2007 | Drew et al. | |
| 2008/0064966 A1 | 3/2008 | Brockway et al. | |
| 2008/0132974 A1 | 6/2008 | Strother et al. | |
| 2008/0171922 A1 | 7/2008 | Teller et al. | |
| 2008/0188762 A1 | 8/2008 | John et al. | |
| 2008/0211665 A1 | 9/2008 | Mazar et al. | |
| 2008/0221633 A1 | 9/2008 | Linker | |
| 2008/0234771 A1* | 9/2008 | Chinchoy et al. | 607/11 |
| 2008/0235469 A1 | 9/2008 | Drew | |
| 2008/0275309 A1 | 11/2008 | Stivoric et al. | |
| 2008/0288030 A1* | 11/2008 | Zhang et al. | 607/62 |
| 2008/0319496 A1 | 12/2008 | Zhu et al. | |
| 2008/0319499 A1 | 12/2008 | Zhu et al. | |
| 2008/0319500 A1 | 12/2008 | Zhu et al. | |
| 2008/0319501 A1 | 12/2008 | Zhu et al. | |
| 2009/0005830 A1 | 1/2009 | Zhu et al. | |
| 2009/0005832 A1 | 1/2009 | Zhu et al. | |
| 2009/0005846 A1 | 1/2009 | Zhu et al. | |
| 2009/0054942 A1 | 2/2009 | Zhu et al. | |
| 2009/0058636 A1 | 3/2009 | Gaskill et al. | |
| 2009/0063193 A1 | 3/2009 | Barton et al. | |
| 2009/0076348 A1 | 3/2009 | Manicka et al. | |
| 2009/0093859 A1 | 4/2009 | Ortega et al. | |
| 2009/0093861 A1 | 4/2009 | Ortega et al. | |
| 2009/0099619 A1 | 4/2009 | Lessmeier et al. | |
| 2009/0105778 A1 | 4/2009 | Lee et al. | |
| 2009/0259272 A1 | 10/2009 | Reddy et al. | |
| 2010/0042176 A1 | 2/2010 | Snell | |
| 2010/0318147 A1 | 12/2010 | Forslund et al. | |
| 2011/0264158 A1 | 10/2011 | Dong et al. | |
| 2011/0264168 A1 | 10/2011 | Dadd et al. | |
| 2011/0307026 A1 | 12/2011 | Zhu et al. | |
| 2011/0319772 A1 | 12/2011 | Ingle | |
| 2011/0319956 A1 | 12/2011 | Zhu et al. | |
| 2012/0041500 A1 | 2/2012 | Zhu et al. | |
| 2012/0041503 A1 | 2/2012 | Zhu et al. | |
| 2013/0261689 A1 | 10/2013 | Zhu et al. | |
| 2013/0261690 A1 | 10/2013 | Ortega et al. | |

FOREIGN PATENT DOCUMENTS

| | | |
|---|---|---|
| EP | 2164560 A1 | 2/2010 |
| WO | WO-0074773 A1 | 12/2000 |
| WO | WO-2005/011475 A2 | 2/2005 |
| WO | WO-2006/068880 A1 | 6/2006 |
| WO | WO-2008063498 A1 | 5/2008 |
| WO | WO-2009/006321 A2 | 1/2009 |
| WO | WO-2009/006325 A1 | 1/2009 |
| WO | WO-2009/006331 A1 | 1/2009 |
| WO | WO-2009/006339 A1 | 1/2009 |
| WO | WO-2009006327 A1 | 1/2009 |
| WO | WO-2009078751 A1 | 6/2009 |
| WO | WO-2010/042910 A1 | 4/2010 |
| WO | WO-2010/071849 A2 | 6/2010 |
| WO | WO-2011/139691 A1 | 11/2011 |
| WO | WO-2012/005985 A2 | 1/2012 |
| WO | WO-2012125273 A2 | 9/2012 |
| WO | WO-2012125273 A3 | 9/2012 |

OTHER PUBLICATIONS

Dong, Y., et al., "His-Bundle Capture Verification and Monitoring", U.S. Appl. No. 61/328,248, filed Apr. 27, 2010, 40 pgs.

Ingle. F., et al., "Lead Motion Sensing Via Cable Microphonics", U.S. Appl. No. 61/359,430, 52 pgs.

US 6,875,206, Apr. 5, 2005, Ponzi, Dean M (withdrawn).

"U.S. Appl. No. 10/004,695, Non-Final Office Action mailed Dec. 22, 2003", 6 pgs.

"U.S. Appl. No. 10/004,695, Notice of Allowance mailed Apr. 13, 2004", 7 pgs.

"U.S. Appl. No. 10/004,695, Response filed Mar. 9, 2004 to Non-Final Office Action mailed Dec. 22, 2003", 8 pgs.

"U.S. Appl. No. 10/745,302, Non-Final Office Action mailed Mar. 14, 2006", 19 pgs.

"U.S. Appl. No. 10/745,302, Non-Final Office Action mailed Sep. 14, 2006", 14 pgs.

"U.S. Appl. No. 10/745,302, Non-Final Office Action mailed Sep. 23, 2005", 11 pgs.

"U.S. Appl. No. 10/745,302, Notice of Allowance mailed Mar. 12, 2007", 4 pgs.

"U.S. Appl. No. 10/745,302, Response filed Jun. 26, 2006 to Non Final Office Action mailed Mar. 14, 2006", 16 pgs.

"U.S. Appl. No. 10/745,302, Response filed Sep. 12, 2005 to Restriction Requirement mailed Aug. 12, 2005", 6 pgs.

"U.S. Appl. No. 10/745,302, Response filed Dec. 14, 2006 to Non Final Office Action mailed Sep. 14, 2006", 13 pgs.

"U.S. Appl. No. 10/745,302, Response filed Dec. 23, 2005 to Non Final Office Action mailed Sep. 23, 2005", 15 pgs.

"U.S. Appl. No. 10/745,302, Restriction Requirement mailed Aug. 12, 2005", 7 pgs.

"U.S. Appl. No. 11/300,242, Final Office Action mailed Aug. 4, 2009", 9 pgs.

"U.S. Appl. No. 11/300,242, Non Final Office Action mailed May 12, 2011", 9 pgs.

"U.S. Appl. No. 11/300,242, Non-Final Office Action mailed Mar. 23, 2008", 8 pgs.

"U.S. Appl. No. 11/300,242, Notice of Allowance mailed Jan. 24, 2012", 5 pgs.

"U.S. Appl. No. 11/300,242, Notice of Allowance mailed May 8, 2012", 6 pgs.

"U.S. Appl. No. 11/300,242, Notice of Allowance mailed Aug. 24, 2012", 7 pgs.

"U.S. Appl. No. 11/300,242, Response filed Feb. 4, 2010 to Final Office Action mailed Aug. 4, 2009", 11 pgs.

"U.S. Appl. No. 11/300,242, Response filed Apr. 2, 2009 to Restriction Requirement mailed Dec. 15, 2008", 8 pgs.

"U.S. Appl. No. 11/300,242, Response filed Sep. 12, 2011 to Non Final Office Action mailed May 12, 2011", 8 pgs.

"U.S. Appl. No. 11/300,242, Response filed Sep. 26, 2008 to Non-Final Office Action mailed Mar. 27, 2008", 10 pgs.

"U.S. Appl. No. 11/300,242, Restriction Requirement mailed Dec. 15, 2008", 10 pgs.

"U.S. Appl. No. 12/147,293, Notice of Allowance mailed Apr. 8, 2011", 12 pgs.

"U.S. Appl. No. 12/147,293, Response filed Feb. 8, 2011 to Restriction Requirement mailed Oct. 8, 2010", 9 pgs.

"U.S. Appl. No. 12/147,293, Restriction Requirement mailed Oct. 8, 2010", 12 pgs.

"U.S. Appl. No. 12/147,339, Notice of Allowance mailed Mar. 30, 2011", 9 pgs.

"U.S. Appl. No. 12/147,339, Notice of Allowance mailed Dec. 22, 2010", 8 pgs.

"U.S. Appl. No. 12/147,339, Response filed Oct. 20, 2010 to Restriction Requirement mailed Oct. 8, 2010", 7 pgs.

"U.S. Appl. No. 12/147,339, Restriction Requirement mailed Oct. 8, 2010", 7 pgs.

"U.S. Appl. No. 12/147,376, Final Office Action mailed Apr. 20, 2011", 11 pgs.

(56) References Cited

OTHER PUBLICATIONS

"U.S. Appl. No. 12/147,376, Non Final Office Action mailed Oct. 3, 2011", 8 pgs.
"U.S. Appl. No. 12/147,376, Non-Final Office Action mailed Sep. 15, 2010", 9 pgs.
"U.S. Appl. No. 12/147,376, Notice of Allowance mailed Mar. 19, 2012", 7 pgs.
"U.S. Appl. No. 12/147,376, Notice of Allowance mailed Aug. 30, 2012", 7 pgs.
"U.S. Appl. No. 12/147,376, Notice of Allowance mailed Dec. 7, 2012", 7 pgs.
"U.S. Appl. No. 12/147,376, Response filed Feb. 15, 2011 to Non Final Office Action mailed Sep. 15, 2010", 9 pgs.
"U.S. Appl. No. 12/147,376, Response filed Feb. 29, 2012 to Non Final Office Action mailed Oct. 3, 2011", 6 pgs.
"U.S. Appl. No. 12/147,376, Response filed Aug. 22, 2011 to Final Office Action mailed Apr. 20, 2011", 8 pgs.
"U.S. Appl. No. 12/147,425, Non-Final Office Action mailed Sep. 15, 2010", 10 pgs.
"U.S. Appl. No. 12/147,425, Notice of Allowance mailed Apr. 19, 2011", 8 pgs.
"U.S. Appl. No. 12/147,425, Response filed Feb. 15, 2011 to Non Final Office Action mailed Sep. 15, 2010", 8 pgs.
"U.S. Appl. No. 12/249,454, Examiner Interview Summary mailed Feb. 22, 2012", 3 pgs.
"U.S. Appl. No. 12/249,454, Final Office Action mailed Nov. 23, 2011", 8 pgs.
"U.S. Appl. No. 12/249,454, Non Final Office Action mailed Apr. 6, 2011", 8 pgs.
"U.S. Appl. No. 12/249,454, Non Final Office Action mailed Sep. 4, 2012", 8 pgs.
"U.S. Appl. No. 12/249,454, Notice of Allowance mailed Dec. 26, 2012", 5 pgs.
"U.S. Appl. No. 12/249,454, Response filed Apr. 2, 2012 to Final Office Action mailed Nov. 23, 2011", 12 pgs.
"U.S. Appl. No. 12/249,454, Response filed Aug. 30, 2011 to Non Final Office Action mailed Apr. 6, 2011", 14 pgs.
"U.S. Appl. No. 12/249,454, Response filed Dec. 4, 2012 to Non Final Office Action mailed Sep. 4, 2012", 12 pgs.
"U.S. Appl. No. 12/249,479, Final Office Action mailed Dec. 2, 2011", 8 pgs.
"U.S. Appl. No. 12/249,479, Non Final Office Action mailed Apr. 5, 2011", 10 pgs.
"U.S. Appl. No. 12/249,479, Non Final Office Action mailed Sep. 4, 2012", 7 pgs.
"U.S. Appl. No. 12/249,479, Notice of Allowance mailed Jan. 8, 2013", 5 pgs.
"U.S. Appl. No. 12/249,479, Response filed Apr. 2, 2012 to Final Office Action mailed Dec. 2, 2011", 9 pgs.
"U.S. Appl. No. 12/249,479, Response filed dec. 4, 2012 to Non Final Office Action mailed Sep. 4, 2012", 9 pgs.
"U.S. Appl. No. 12/249,479, Response filed Aug. 30, 2011 to Non Final Office Action mailed Apr. 5, 2011", 12 pgs.
"U.S. Appl. No. 13/094,416, Non Final Office Action mailed Dec. 14, 2012", 13 pgs.
"U.S. Appl. No. 13/094,416, Notice of Allowance mailed Jun. 25, 2013", 8 pgs.
"U.S. Appl. No. 13/094,416, Response filed Apr. 15, 2013 to Non Final Office Action mailed Dec. 14, 2012", 14 pgs.
"U.S. Appl. No. 13/094,416, Response filed Sep. 17, 2012 to Restriction Requirement mailed Aug. 16, 2012", 8 pgs.
"U.S. Appl. No. 13/094,416, Restriction Requirement mailed Aug. 16, 2012", 5 pgs.
"U.S. Appl. No. 13/211,937, Non Final Office Action mailed Jan. 15, 2013", 7 pgs.
"U.S. Appl. No. 13/211,937, Notice of Allowance mailed May 13, 2013", 6 pgs.
"U.S. Appl. No. 13/211,937, PTO Response to 312 Communication mailed Aug. 20, 2013", 2 pgs.
"U.S. Appl. No. 13/211,937, Response filed Apr. 11, 2013 to Non Final Office Action mailed Jan. 15, 2013", 8 pgs.
"U.S. Appl. No. 13/217,776, Non Final Office Action mailed Jan. 15, 2013", 6 pgs.
"U.S. Appl. No. 13/217,776, Notice of Allowance mailed May 15, 2013", 6 pgs.
"U.S. Appl. No. 13/217,776, Response filed Apr. 11, 2013 to Non Final Office Action mailed Jan. 15, 2013", 9 pgs.
"U.S. Appl. No. 13/688,859, Final Office Action mailed Oct. 8, 2013", 5 pgs.
"U.S. Appl. No. 13/688,859, Response filed Sep. 20, 2013 to Non Final Office Action mailed Jun. 20, 2013", 12 pgs.
"European Application Serial No. 08772198.1, Office Action mailed Sep. 13, 2010", 6 pgs.
"European Application Serial No. 08772198.1, Response filed Mar. 31, 2011 to Communication mailed Sep. 30, 2010", 11 pgs.
"European Application Serial No. 08781107.1, Invitation Pursuant to Rule 63(1) EPC mailed Jul. 13, 2010", 3 pgs.
"European Application Serial No. 08781107.1, Communication dated Feb. 9, 2010", 2 pgs.
"European Application Serial No. 08781107.1, Extended European Search Report mailed Nov. 25, 2010", 6 pgs.
"European Application Serial No. 08781107.1, Response filed Mar. 5, 2010 to Communication dated Feb. 9, 2010", 2 pgs.
"European Application Serial No. 08781107.1, Response filed Jun. 14, 2011 to Communication mailed Dec. 14, 2010", 10 pgs.
"European Application Serial No. 08781107.1, Response filed Sep. 22, 2010 to the Invitation to Rule 63(1)", 11 pgs.
"International Application Serial No. PCT/US2005/045044, Written Opinion mailed May 2, 2006", 3 pgs.
"International Application Serial No. PCT/US2008/068618, International Search Report mailed Nov. 26, 2008", 2 pgs.
"International Application Serial No. PCT/US2008/068618, Written Opinion mailed Nov. 26, 2008", 6 pgs.
"International Application Serial No. PCT/US2008/068630, International Search Report mailed Sep. 10, 2008", 1 pg.
"International Application Serial No. PCT/US2008/068630, Written Opinion mailed Sep. 10, 2008", 4 pgs.
"International Application Serial No. PCT/US2008/068635, International Search Report mailed Sep. 9, 2008", 3 pgs.
"International Application Serial No. PCT/US2008/068635, Written Opinion mailed Sep. 9, 2008", 4 pgs.
"International Application Serial No. PCT/US2008/068647, International Search Report mailed Sep. 22, 2008", 2 pgs.
"International Application Serial No. PCT/US2008/068647, Written Opinion mailed Sep. 22, 2008", 4 pgs.
"International Application Serial No. PCT/US2011/033944, International Search Report mailed Sep. 8, 2011", 5 pgs.
"International Application Serial No. PCT/US2011/033944, Written Opinion mailed Sep. 8, 2011", 9 pgs.
"International Application Serial No. PCT/US2012/026571, International Preliminary Report on Patentability mailed Sep. 26, 2013", 9 pgs.
"International Application Serial No. PCT/US2012/026571, International Search Report mailed Oct. 18, 2012", 4 pgs.
"International Application Serial No. PCT/US2012/026571, Written Opinion mailed Oct. 18, 2012", 7 pgs.
Al-Khadra, A., et al., "The Role of Electroporation in Defibrillation", Circulation Research, 87(9), (Oct. 2000), 797-804.
Avitall, B., et al., "Iontophoretic Transmyocardial Drug Delivery. A Novel Approach to Antiarrhythmic Drug Therapy", Circulation, 85(4), (1992), 1582-1593.
Barba-Pichardo, Rafael, et al., "Permanent His-Bundle Pacing in Patients With Infra-Hisian Atrioventricular Block", Rev Esp Cardiol. 59(6), (Mar. 9, 2006), 553-558.
Bonanno, C., et al., "Effect on QRS Duration and Feasibility of Septal and Multisite Right Ventricular Pacing", Cardiostimolazione, 14(3), (Abstract Only), (Sep. 1996), p. 195.
Buckingham, Thomas A., et al., "Acute Hemodynamic Effects of Atrioventricular Pacing at Differing Sites in the Right Ventricle Individually and Simultaneously", PACE, 20[Pt. I], (Apr. 1997), 909-915.

(56) References Cited

OTHER PUBLICATIONS

Cantu, F., et al., "Validation of Criteria for Selective His Bundle and Para-Hisian Permanent Pacing", PACE, vol. 29, (Dec. 2006), 1326-1333.

Cantu, Francesco, et al., "A Methodical Approach to Validate Selective His Bundle and para-Hisian Permanent Pacing", [abstract] Oasis, (2006), 1 pg.

Catanzariti, Domenico, et al., "Permanent His Bundle Pacing Does Not Induce Ventricular Dyssynchrony. An Echocardiographic Intrapatient Study of Comparison with Conventional Pacing", [abstract] Oasis, (2006), 1 pg.

Chudzik, Michal, "Ventricular Endocardial Right Bifocal Stimulation in Treatment of Severe Dilated Cardiomyopathy Heart Failure in Patients with Unsuccessful Biventricular Pacemaker Implantation", [abstract CP07] Europace Supplements, vol. 7, (May 2005), 1 pg.

Deshmukh, P., et al., "Permanent, Direct His-Bundle Pacing: A Novel Approach to Cardiac Pacing in Patients With Normal His-Purkinje Activation", Circulation, 101(8), (Feb. 29, 2000), 869-877.

Deshmukh, Pramod M., et al., "Direct His-Bundle Pacing: Present and Future", PACE, vol. 27, Part II, (Jun. 2004), 862-870.

El-Sherif, N., et al., "Normalization of Bundle Branch Block Patterns by Distal His Bundle Pacing: Clinical and Experimental Evidence of Longitudinal Dissociation in the Pathologic His Bundle", Circulation, 57(3), (Mar. 1978), 473-483.

Flynn, David M, et al., "Extendable and Retractable Lead Having a Snap-Fit Terminal Connector", U.S. Appl. No. 11/173,664, filed Jul. 1, 2005, 53 pgs.

Golia, P., et al., "Multisite Pacing of Right Ventricle in Heart Failure: Echocardiographic Evaluation", [Abstract] Cardiostimolazione, vol. 14, No. 3, (Sep. 1996), 5 pgs.

Grosfeld, M. J.W., et al., "Testing a New Mechanism for Left Interventricular Septal Pacing: The Transseptal Route", Europace, vol. 4, (Oct. 2002), 439-444.

Hummel, J. D., et al., "Augmentation of Cardiac Output by Anodal Pacing", [Abstract] Circulation, 90(No. 4, Part 2), (Oct. 1994), p. I-69.

Kamboh, A M, et al., "Area-Power Efficient VLSI Implementation of Multichannel DWT for Data Compression in Implantable Neuroprosthetics", IEEE Transactions on Biomedical Circuits and Systems, 1(2), (Jun. 2007), 128-135.

Kamen, P. W, et al., "Poincaré plot of heart rate variability allows quantitative display of parasympathetic nervous activity in humans.", Clin Sci (Lond), 91(2), (Aug. 1996), 201-8.

Kanno, S., et al., "Establishment of a simple and practical procedure applicable to therapeutic angiogenesis", Circulation, 99(20), (May 25, 1999), 2682-2687.

Kavanagh, K. M., et al., "Monophasic Versus Biphasic Cardiac Stimulation: Mechanism of Decreased Energy Requirements", PACE, vol. 13, No. 10, (Oct. 1990), 10 pgs.

Kaye, D. M., et al., "Frequency-dependent activation of a constitutive nitric oxide synthase and regulation of contractile function in adult rat ventricular myocytes", Circulation Research, 78(2), (Feb. 1996), 217-24.

Khandoker, A. H, et al., "Identifying diabetic patients with cardiac autonomic neuropathy by heart rate complexity analysis", BioMedical Engineering OnLine, 8(3), (2009), 12 pgs.

Knapp, C. P, et al., "Snap Fit Terminal Connector", U.S. Appl. No. 09/184,226, filed Nov. 2, 1998, 39 pgs.

Kumar, Sunil, et al., "Ubiquitous computing for remote cardiac patient monitoring: a survey.", International Journal of Telemedicine and Applications, vol. 2008, Article ID 459185, (2008), 19 pgs.

Kutarski, A., et al., "Factors Influencing Differences of RVA & RVOT Pacing Hemodynamic Effects", [abstract CP05] Europace Supplements, vol. 7, (May 2005), p. 288.

Kutarski, A., et al., "Right Ventricular Outflow Tract and Dual Site Right Ventricular Pacing—The Comparison With Apex Pacing", [abstract CP08] Europace Supplements, vol. 7, (May 2005), p. 288.

Labhasetwar, V., et al., "Iontophoresis for Modulation of Cardiac Drug Delivery in Dogs", Proc. Natl. Acad.Sci. USA, 92(7), (Mar. 28, 1995), 2612-2616.

Lazarus, A., et al., "Reduction in Energy Pacing Thresholds by Overlapping Biphasic Stimulation Versus Conventional Bipolar Pacing", PACE, vol. 21, (Nov. 1998), 6 pgs.

Lewicke, A., et al., "Analysis of Heart Rate Variability for Predicting Cardiorespiratory Events in Infants", Accepted Journal—IEEE Transactions on Biomedical Engineering, This one has not been published yet by the IEEE, (2006), 1 pg.

Lewicke, A., et al., "Heart Rate Variability Among Infants Who Have Cardio-Respiratory Events", Pediatric Academic Society, Abstract, (Sep. 2006), 1 pg.

Lewicke, A., et al., "Heart rate variability for predicting cardiorespiratory events in infants", Journal of Electrocardiology, 39(4), Supplement, (Oct. 2006), S83.

Manolis, Antonis S., "The Deleterious Consequences of Right Ventricular Apical Pacing: Time to Seek Alternate Site Pacing", PACE, vol. 29, (Mar. 2006), 298-315.

Mansourati, J., et al., "Left ventricular-based pacing in patients with chronic heart failure: comparison of acute hemodynamic benefits according to underlying heart disease", Eur J Heart Fail., 2(2), (Jun. 2000), 195-9.

Mond, Harry G., et al., "The Right Ventricular Outflow Tract: The Road to Septal Pacing", PACE, vol. 30, (Apr. 2007), 482-491.

Morina-Vazquez, Pablo, et al., "Cardiac Resynchronization Through Selective His Bundle Pacing in a Patient with the So-Called InfraHis Atrioventricular Block", PACE, vol. 28, (Jul. 2005), 726-729.

Occhetta, E., et al., "Prevention of Ventricular Desynchronization by Permanent Para-Hisian Pacing After Atrioventricular Node Ablation in Chronic Atrial Fibrillation: A Crossover, Blinded, Randomized Study Versus Apical Right Ventricular Pacing", Journal of the American College of Cardiology, 47(10), (May 16, 2006), 1938-1945.

Padeletti, Luigi, et al., "Physiologic Pacing: New Modalities and Pacing Sites", PACE, vol. 29, Supplement 2, (Dec. 2006), S73-S77.

Pastore, G., et al., "Different Degree of Ventricular Dyssyncrony Induced by Right Apical, Hissian and Para Hissian Ventricular Pacing", [abstract] Oasis, (2006), 1 pg.

Pastore, Gianni, et al., "Direct His-Bundle Pacing Preserves the Normal Left Activation Sequence: An Acute Echocardiographic Study", [abstract] Oasis, (2006), 1 pg.

Qu, J, et al., "HCN2 overexpression in newborn and adult ventricular myocytes: distinct effects on gating and excitability", Circ. Res., vol. 89(1), (Jul. 6, 2001), e8-14.

Qu, J, et al., "Sympathetic innervation alters activations of pacemaker current (If) in rat ventricle", J. Physiol, 526 Pt 3, (Aug. 1, 2000), 561-569.

Reddy, G. S., "Bundle of His Stimulation System", U.S. Appl. No. 61/045,168, filed Apr. 15, 2008, 37 pgs.

Scheinman, M. M., et al., "Long-Term His-Bundle Pacing and Cardiac Function", Circulation, 101(8), (2000), 836-837.

Schoenfeld, M. H., "Alternative Site Pacing to Promote Cardiac Synchrony: Has Conventional Pacing Become Unconventional?", Journal of the American College of Cardiology, 47(10), (2006), 1946-1948.

Shi, W, et al., "Distribution and prevalence of hyperpolarization-activated cation channel (HCN) mRNA expression in cardiac tissues", Circ. Res., vol. 85(1), (Jul. 9, 1999), e1-6.

Sotobata, I., et al., "Population distribution of Frank-vectorcardiographic measurements of healthy Japanese men", Japanese Circulation Journal, 39(8), (1975), 895-903.

Strydis, Christos, et al., "Profiling of lossless-compression algorithms for a novel biomedical-implant architecture", http://ce.et.tudelft.nl/publicationfiles/1537_555_p109-strydis.pdf, Delft University of Technology, Delft, Netherlands International Conference on Hardware Software Codesign; Proceedings of 6th IEEE/ACM/IFIP international conference on Hardware/Software codesign and system synthesis. Atlanta, GA,Session: Exploration, prof, (2008), 109-114.

Takatsuki, et al., "Clinical Implications of "pure" Hisian pacing in addition to para-Hisian pacing for the diagnosis of supraventricular tachycardia", Heart Rhythm 3 (12), (Dec. 8, 2006), 1412-1418.

Thakral, A, et al., "Effects of anodel vs. cathodal pacing on the mechanical performance of the isolated rabbit heart", J. Appl Physiol., 89(3), (Sep. 2000), 1159-64.

(56) References Cited

OTHER PUBLICATIONS

Tse, Hung-Fat, et al., "Selection of Permanent Ventricular Pacing Site: How Far Should We Go?", Journal of the American College of Cardiology, 48(8), (Sep. 26, 2006), 1649-1651.

Van Gelder, B. M., et al., "Hemodynamic Effect of RV Apex vs RV Septum Pacing in a Monoventricular and Biventricular Configuration in Patients with Heart Failure", [abstract CP06] Europace Supplements, vol. 7, (May 2005), p. 288.

Victor, F., et al., "A Randomized Comparison of Permanent Septal Versus Apical Right Ventricular Pacing: Short-Term Results", Journal of Cardiovascular Electrophysiology, 17(3), (Mar. 2006), 238-242.

Winckels, S. K. G., et al., "High-Septal Pacing Reduces Ventricular Electrical Remodeling and Proarrhythmia in Chronic Atrioventricular Block Dogs", Journal of the American College of Cardiology, 50(9), (Aug. 28, 2007), 906-913.

Yu, H., et al., "MinK-related peptide 1: A beta subunit for the HCN ion channel subunit family enhances expression and speeds activation", Circ. Res., 88(12), (Jun. 22, 2001), e84-7.

Zanon, F., et al., "A Feasible Approach for Direct His-Bundle Pacing Using a New Steerable Catheter to Facilitate Precise Lead Placement", Journal of Cardiovascular Electrophysiology, 17(1), (Jan. 2006), 29-33.

Zanon, Francesco, et al., "A New Technique for Direct His-Bundle Pacing: Acute and Mid-Term Electrical Data Results", [abstract] Oasis, (2006), 1 pg.

Zanon, Francesco, et al., "Direct His Bundle Pacing Preserves Coronary Perfusion Compared With Right Ventricular Apical Pacing: A Prospective, Cross-Over Mid-Term Study", Europace, vol. 10, (2008), 580-587.

Zhang, Y., et al., "His Electrogram Alternans Reveal Dual-Wavefront Inputs Into and Longitudinal Dissociation Within the Bundle of His", Circulation, 104(7), (2001), 832-838.

\* cited by examiner

HIS CAPTURE VERIFICATION USING ELECTRO-MECHANICAL DELAY

CROSS REFERENCE TO RELATED APPLICATIONS

This application claims benefit of priority under 35 U.S.C. 119(e) to Maskara et al., U.S. Provisional Patent Application Ser. No. 61/452,412, entitled "His Capture Verification Using Electro-mechanical Delay", filed on Mar. 14, 2011, which is hereby incorporated herein by reference in its entirety.

BACKGROUND

A medical device can be implanted in a body to perform one or more tasks including monitoring, detecting, or sensing physiological information in or otherwise associated with the body, diagnosing a physiological condition or disease, treating or providing a therapy for a physiological condition or disease, or restoring or otherwise altering the function of an organ or a tissue. Examples of an implantable medical device can include a cardiac rhythm management device, such as a pacemaker, a cardiac resynchronization therapy device, a cardioverter or defibrillator, a neurological stimulator, a neuromuscular stimulator, or a drug delivery system.

In various examples, cardiac rhythm or function management devices can sense intrinsic heart contractions, deliver pacing pulses to evoke responsive heart contractions, or deliver a shock to interrupt certain arrhythmias. In certain examples, one or more of these functions can help improve a patient's heart rhythm or can help coordinate a spatial nature of a heart contraction, either of which can improve cardiac output of blood to help meet the patient's metabolic need for such cardiac output.

Some cardiac rhythm or function management devices can be configured to deliver energy at or near the His bundle to achieve pacing via natural conduction pathways, such as via Purkinje fiber conduction of electrical impulses. Various methods for verification of cardiac capture have been proposed. For example, Zhu et al. PCT Patent Publication No. WO 2010/071849, entitled DEVICES, METHODS, AND SYSTEMS INCLUDING CARDIAC PACING, which is incorporated herein by reference in its entirety, refers to determining the effectiveness or completeness of His-bundle capture using attributes of a QRS signal, such as QRS narrowing, or using mechanical or hemodynamic sensors.

Dong et al. U.S. Patent Application No. 61/328,248 entitled HIS-BUNDLE CAPTURE VERIFICATION AND MONITORING, which is incorporated by reference herein in its entirety, refers to His-bundle capture verification using hemodynamic sensors such as heart sound or blood pressure sensors.

OVERVIEW

The efficiency of a cardiac response to artificial pacing can depend on many factors, including how and where pacing is performed. An efficient pacing technique, at least in terms of cardiac output, can include pacing at the His-bundle. Pacing at the His-bundle can activate the heart's natural conduction mechanisms, such as the left and right branch bundles and Purkinje fibers, producing an efficient and coordinated cardiac response.

This document describes, among other things, systems, methods, machine-readable media, or other techniques that can involve stimulating a His-bundle at a first time, receiving cardiac activity information from other than an intrinsic heart signal, computing a time interval, and using the time interval to provide a cardiac stimulation diagnostic indication, such as an indication of cardiac capture via His-bundle stimulation.

The techniques can involve detecting intrinsic and non-intrinsic cardiac activity, such as using a plurality of sensors to detect electrical or mechanical cardiac events. Using timing information associated with detected cardiac activity, discrimination between Purkinje fiber cardiac capture, cell-to-cell conduction cardiac capture, and intrinsic conduction cardiac contractions can be provided in an automated fashion, such as without analysis of QRS waveforms.

The present inventors have recognized, among other things, that a problem to be solved can include providing verification of cardiac capture in response to His-bundle stimulation. Verification of cardiac capture can be shown by QRS narrowing, an attribute that can be discerned from multi-axis ECG data. However, multi-axis ECG data are often not available to an implanted medical device. In an example, the present subject matter can provide a solution to the capture verification problem, such as by measuring time intervals between paced and sensed cardiac events. In an example, a single sensor can be used to provide cardiac activity information and related interval information. The interval information can be compared to a threshold value to provide cardiac diagnostic information, including cardiac capture verification information.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Stimulation energy can be provided to a His-bundle to activate natural, coordinated cardiac contraction mechanisms. Interval information, such as can describe a response to an application of His-bundle stimulation energies, can provide cardiac stimulation diagnostic information. For example, interval information can be used to discriminate between intrinsic conduction cardiac contractions and contractions in response to His-bundle pacing.

A natural conduction pathway of the heart that can activate cardiac contractions originates in the sinoatrial (SA) node in the right atrium of the heart. Intrinsic electrical impulses, generated at the SA node, can trigger the atria to contract. From the SA node, a conduction pathway leads electrical impulses to the atrioventricular (AV) node, located between the atrium and the ventricle. Following a delay at the AV node, conduction can continue through the His-bundle to the left and right bundle branches, then to the Purkinje fibers and the apex of the heart, and finally up and around to the ventricular myocardium to produce a coordinated cardiac contraction, such as of both the left and right ventricles.

Cardiac contractions using a natural conduction pathway, such as intrinsic contractions, can be faster and more efficient than paced contractions, such as via apical or biventricular pacing. Accordingly, providing stimulation energy (e.g., a pacing energy) to a portion of the natural conduction pathway, such as a His-bundle, can activate the faster-conducting fibers, such as the Purkinje fibers, to provide more efficient physiological stimulation and potentially better hemodynamic benefits to a subject.

In an example, left bundle branch block (LBBB) can be due to a blockage located in the His-bundle. In such a scenario, cardiac resynchronization therapy with a single lead at the His-bundle, distal to the blockage or defect, can be more effective than traditional biventricular pacing. However, His-bundle pacing may have higher activation thresholds and may be more susceptible to small changes in lead positioning.

Figure 1:
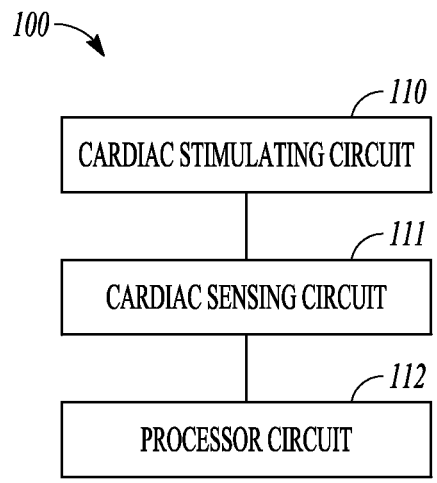
FIG. 1 illustrates generally an example of a system including a cardiac stimulating circuit, a cardiac sensing circuit, and a processor.

FIG. 1 illustrates generally an example of a system 100 that can include a cardiac stimulating circuit 110, a cardiac sensing circuit 111, and a processor circuit 112. In an example, the cardiac stimulating circuit 110 can be configured to generate a stimulation energy configured to invoke a cardiac depolarization. In an example, the stimulation energy can be configured to provide His-bundle stimulation. His-bundle stimulation can be provided, for example, from the right ventricle at one or more locations along the interventricular septum, the right ventricular outflow tract septum, the right atrium, or one or more other locations near the His-bundle.

In an example, the cardiac sensing circuit 111 can be configured to receive electrical information from the heart, for example, over at least a portion of the cardiac cycle. In an example, the electrical information can include an electrical cardiogram (ECG) signal (e.g., an evoked response, a subcutaneous ECG, or other), an electrical signal from a heart sound sensor such as a microphone, an electrical signal from an accelerometer configured to provide an indication of mechanical cardiac activity, an electrical signal from a pressure sensor configured to provide an indication of a pressure, such as a central venous pressure (CVP), or one or more other electrical signals indicative of cardiac information (e.g., thoracic impedance).

The processor circuit 112 can be configured to determine a characteristic of the received electrical information from the heart over at least a portion of the cardiac cycle using the received electrical information. In an example, the characteristics can include at least one of:

(1) a width, amplitude, slope, or latency of a QRS complex;
(2) a pressure;
(3) an indication of mechanical motion provided by an accelerometer; or
(4) an impedance.

In an example, one or more other characteristics can be used, such as a measure of contractility, synchrony, or cardiac output, among others. In an example, characteristics can include QRS axis/polarity or repolarization index information (e.g., T-wave polarity, measures or surrogate measures of repolarization time, etc.), or an indication of QRS axis deviation, such as can be provided by an array of electrodes disposed on or in a body.

Information from the determined characteristics can be used to calculate a time interval. For example, a first time interval can indicate an intrinsic AH delay, the time from a sensed event in the atrium to the arrival of an electrical signal at the His-bundle. A second time interval can indicate the time from a sensed cardiac event, such as an atrial contraction, to LV $dP/dt_{max}$, the time at which the left ventricle reaches a maximum pressure. Numerous additional or alternative other intervals can be measured, such as using the electrode and sensor configurations described in FIGS. 3, 4, and 5.

In an example, the processor circuit 112 can be configured to provide a cardiac stimulation diagnostic indication using the determined characteristic or interval, such as using a detected change in the determined characteristic or interval, or comparing the determined characteristic or interval to a threshold. For example, the processor circuit 112 can provide a cardiac stimulation diagnostic indication using a cardiac stimulation diagnostic metric. In an example, the cardiac stimulation diagnostic indication can be used to discriminate between His-bundle cardiac capture via Purkinje fiber conduction, cell-to-cell conduction cardiac capture, and intrinsic conduction cardiac contraction, such as using the systems and methods described below.

In an example, the processor circuit 112 can be configured to report (or make available) one or more cardiac stimulation diagnostic indications to an external module (e.g., an external programmer, directly to a clinician's handheld mobile device, email, etc.). In an example, the processor circuit 112 can be configured to provide a cardiac stimulation diagnostic indication for a plurality of cardiac cycles, count or store one or more of the results from the classification, such as in a histogram, and, when the His-bundle capture percentage is below a threshold, the processor can be configured to do one or more of the following:

(1) provide an alert to an external module;
(2) reduce the stimulation energy to save power;
(3) increase the stimulation energy (e.g., the pacing threshold) to ensure His-bundle capture;
(4) switch to a different pacing configuration (e.g., different pacing waveform, site, etc.); or
(5) initiate a test to determine the His-bundle threshold.

In certain examples, the percentage of the His-bundle capture can be trended and the trending can be provided to an external module and displayed to the user.

In an example, the processor circuit 112 can be configured to increase the stimulation energy (e.g., the pacing threshold) to increase the His-bundle capture percentage. In certain examples, the stimulation energy can be increased after a time interval (e.g., a number of hours, days, etc.), after a number of cardiac cycles, after a number of His-bundle captures, after a number of His-bundle non-captures, or at a threshold His-bundle capture percentage, among other times.

Figure 2:
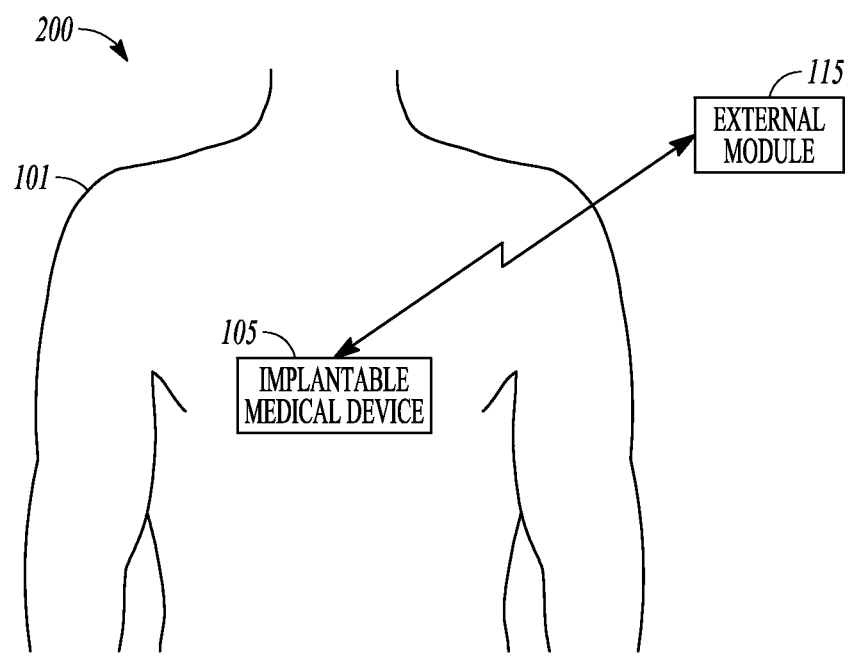
FIG. 2 illustrates generally an example of a system including an implantable medical device (IMD) in a subject, the IMD wirelessly coupled to an external module.

FIG. 2 illustrates generally an example of a system 200 including an ambulatory or implantable medical device (IMD) 105 in a subject 101, the IMD 105 wirelessly coupled to an external module 115. In an example, the IMD 105 can include one or more of the cardiac stimulating circuit 110, the cardiac sensing circuit 111, or the processor circuit 112. In certain examples, a portion of the functionality of one or more of the cardiac stimulating circuit 110, the cardiac sensing circuit 111, or the processor circuit 112 can occur in the IMD 105, and another portion elsewhere (e.g., in an external component, such as a 12-lead ECG).

In an example, the IMD 105 can include a pacemaker, a defibrillator, or one or more other implantable medical devices. In an example, the IMD 105 can include an antenna configured to provide radio-frequency or other communication between the IMD 105 and the external module 115, or other external device. In an example, the external module 115 can include an antenna. In an example, the external module 115 can include a local medical device programmer or other local external module, such as within wireless communication range of the IMD 105 antenna. The external module 115 can include a remote medical device programmer or one or more other remote external modules (e.g., outside of wireless communication range of the IMD 105 antenna, but coupled to the IMD 105 using a local external device, such as a repeater or network access point). In an example, the external module 115 can be configured to send information to or receive information from the IMD 105. The information can include medical device programming information, subject data, device data, or other instructions, alerts, or other information. In an example, the external module 115 can be configured to display information (e.g., received information) to a user. Further, the local programmer or the remote programmer can be configured to communicate the sent or received information to a user or physician, such as by sending an alert via email of the status of the subject 101 or the system 200 components.

Figure 3:
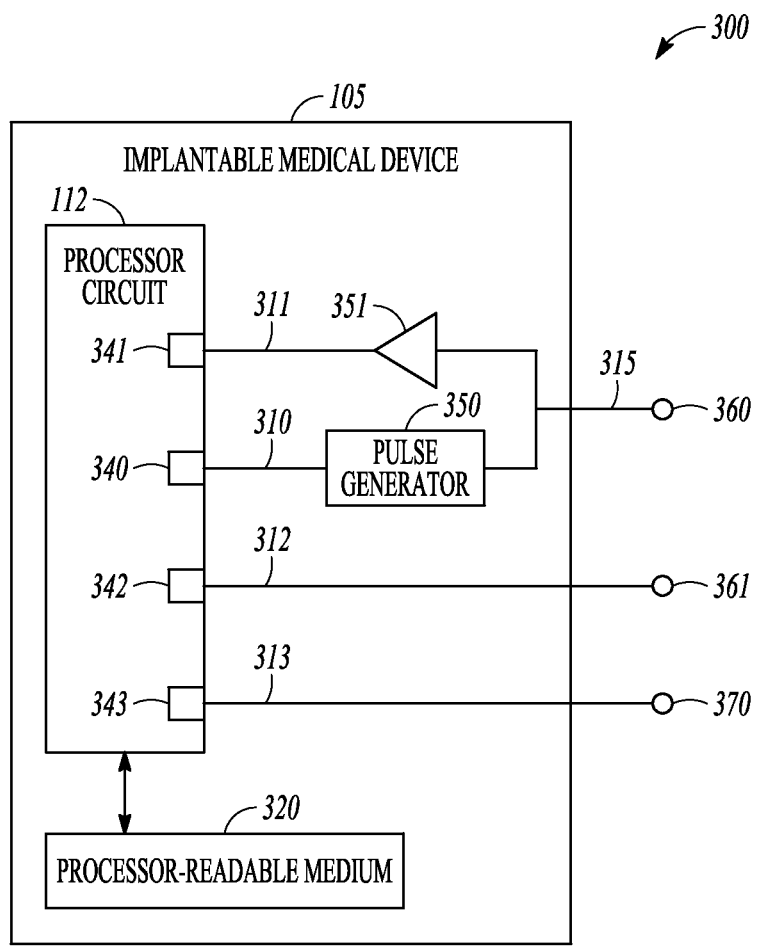
FIG. 3 illustrates generally an example of a portion of an IMD for delivering cardiac therapy and monitoring cardiac activity.

FIG. 3 illustrates generally an example of a system 300 for delivering stimulation energy to a subject or sensing a subject response. In an example, the system 300 can include an IMD 105, the IMD 105 including systems configured to deliver stimulation energy to a subject, or receive information about physiological activity. In an example, the system 300 can include several pacing and sensing channels, such as a right ventricular pacing channel 310, a left ventricular pacing channel 312, a right ventricular sensing channel 311, or a sensor sensing channel 313. In an example, the system 300 can include a processor circuit 112, and a processor-readable medium 320, such as can be accessed using the processor circuit 112.

In an example, the processor circuit 112 can include a plurality of data inputs and outputs. For example, a first data output 340 can be coupled to the right ventricular pacing channel 310, such as to provide control information to a pulse generator 350. The pulse generator 350 can be coupled to an electrode 360 disposed on a lead 315 or elsewhere. A first data input 341 can be coupled to the right ventricular sensing channel 311, such as to receive, via a sense amplifier 351, an electrical signal from the electrode 360. In an example, the electrode 360 can be configured to be located in a right ventricle, such as in the septal region proximal to the His-bundle, the right ventricular outflow tract, the free wall region, or another region of the right ventricle.

In an example, a second data output 342 can be coupled to the left ventricular pacing channel 312, such as can be coupled to an electrode 361 via lead 312. A second data input 343 can be coupled to a first sensor 370, such as a pressure sensor configured to be disposed in a thoracic vena cava, such as to measure central venous pressure to provide an indication of a right atrial pressure. In an example, the processor circuit 112 can receive pressure information via an electrical signal and can interpret the pressure signal, such as using instructions provided on the processor-readable medium 320.

In an example, the system 300 and the IMD 105 can include several additional pacing or sensing channels, such as an atrial pacing channel, an internal thoracic pacing or sensing channel configured to couple the processor circuit 112 to an internal thoracic location external to the heart (e.g., through one or more leads, electrodes, pulse generators, or sense amplifiers), or one or more other atrial or ventricular pacing or sensing channels, among others. The system 300 can include several additional sensing channels, configured to receive information from sensors such as accelerometers, pressure sensors, or electrodes configured to measure electric field information. In an example, the IMD 105 can include one or more other right or left ventricular sensing or pacing channels, such as a right ventricular apex backup pacing channel.

In the example of FIG. 3, the processor circuit 112 can be an implantable component, an external component, or a combination or permutation of an implantable processor and an external processor. In an example, if at least a portion of the processor circuit 112 includes an external processor, then the processor circuit 112 can be configured to be communicatively coupled (such as via telemetry, RF, or other communication protocol) with the remaining implantable components such as the sense amplifier 351, the pulse generator 350, or the processor-readable medium 320. In an example, the implantable processor can be configured to have reduced or minimal functionality or power consumption. In some examples, it can be advantageous for the processor circuit 112 to include an external processor for computing complex operations or to store large amounts of information. In an example, the processor circuit 112 can include a microcontroller, a microprocessor, a logic circuit, or other processor. In an example, the cardiac stimulation circuit 110 can include the pulse generator 350, and the cardiac sensing circuit 111 can include the sense amplifier 351.

Figure 4:
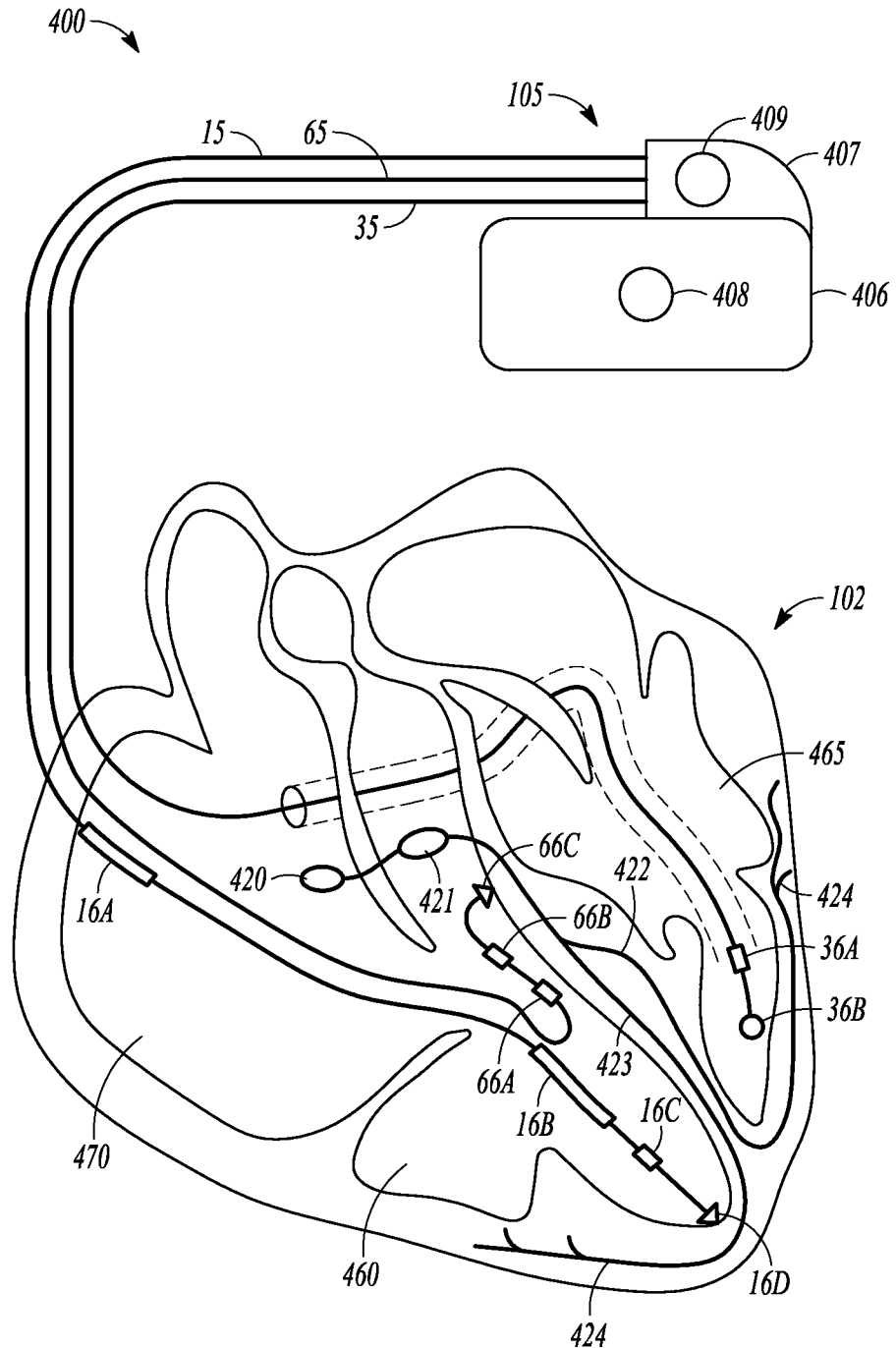
FIG. 4 illustrates generally an example of a system or portion of a system for delivering cardiac therapy or monitoring cardiac activity.

FIG. 4 illustrates generally an example of a system 400 including an IMD 105, a right ventricular apex lead 15, a left ventricular lead 35, and a right ventricular septum lead 65. The IMD 105 can include a housing 406 (or CAN) and a header 407. In an example, at least a portion of the exterior of the housing 406 or the header 407 can include an electrode, such as a housing can electrode 408, or a header electrode 409.

The right ventricular apex lead 15 can include a first electrode 16A configured to be located in the superior vena cava of a heart 102, and a second electrode 16B, a third electrode 16C, and a fourth electrode 16D configured to be located in the right ventricle 460 of the heart 102. In an example, the first electrode 16A can include a proximal defibrillation coil electrode, or the second electrode 16B can include a distal defibrillation coil electrode, such as can be configured to deliver a high energy shock (e.g., 0.1 Joule or greater) to the heart.

The left ventricular lead 35 can include a fifth electrode 36A and a sensor 36B configured to be located in, on, or near the left ventricle 465 of the heart 102, such as within the coronary vasculature. In an example, the sensor 36B can include a distal pacing or sensing electrode, or a pressure sensor. The right ventricular septum lead 65 can include a sixth electrode 66A, an seventh electrode 66B, and a eighth electrode 66C configured to be located along the septum in the right ventricle 460 of the heart 102. In an example, the right ventricular septum lead 65 can be configured to provide His-bundle pacing along the septum wall. In an example, the housing can electrode 408 can be electrically coupled to at least one other electrode (e.g., the first electrode 16A), or the housing can electrode 408 can be electrically isolated from other electrodes and capable of independent control. In an example, the first electrode 16A through the eighth electrode 66C can include at least one of a coil-type electrode, a ring-type electrode, or a tip electrode.

In an example, the right ventricular apex lead 15 can be configured to electrically couple the IMD 105 to at least one of the right ventricle 460, the right atrium 470, or the superior vena cava using at least one electrode (e.g., the first electrode 16A, the second electrode 16B, the third electrode 16C, or the fourth electrode 16D), the left ventricular lead 35 can be configured to electrically couple the IMD 105 to the left ventricle 465 using at least one electrode (e.g., the fifth electrode 36A or the sensor 36B), or the right ventricular septum lead 65 can be configured to electrically couple the IMD 105 to the interventricular septum using at least one electrode (e.g., the sixth electrode 66A, the seventh electrode 66B, or the eighth electrode 66C). In an example, at least one of the second electrode 16B, the third electrode 16C, or the fourth electrode 16D, can be configured to be located in, on, or near a right apical region of the heart 102. In other examples, the fifth electrode 36A or the sensor 36B can be configured to be located in, on, or near a left apical region of the heart 102 or a left ventricular free lateral wall of the heart 102. In an example, a cardiac rhythm management device capable of delivering defibrillation energy can include a shocking electrode, such as the first electrode 16A, electrically tied or coupled to the housing can electrode.

FIG. 4 illustrates several of the natural conduction systems of the heart. For example, the eighth electrode 66C is located near the His-bundle 421 and the AV node 420. The His-bundle is coupled to the left branch bundle 422 and the right branch bundle 423. Each of the left and right branch bundles leads to the Purkinje fibers 424 near the apex of the heart 102. In an example, the system 400 can include a plurality of sensors configured to detect cardiac activity, such as an intrinsic cardiac contraction via Purkinje fiber conduction. For example, the system 400 can include an accelerometer, or other sensor configured to detect heart sound information. The system 400 can include one or more pressure sensors, such as can be disposed in one of the atria or ventricles, or a vein or sinus, such as to provide timing information regarding the opening and closing of the heart valves. In an example, a pressure sensor disposed in the thoracic vena cava near the right atrium can indirectly provide information about left ventricular pressure. In an example, the pressure sensors can be wirelessly coupled to the IMD 105.

Figure 5:
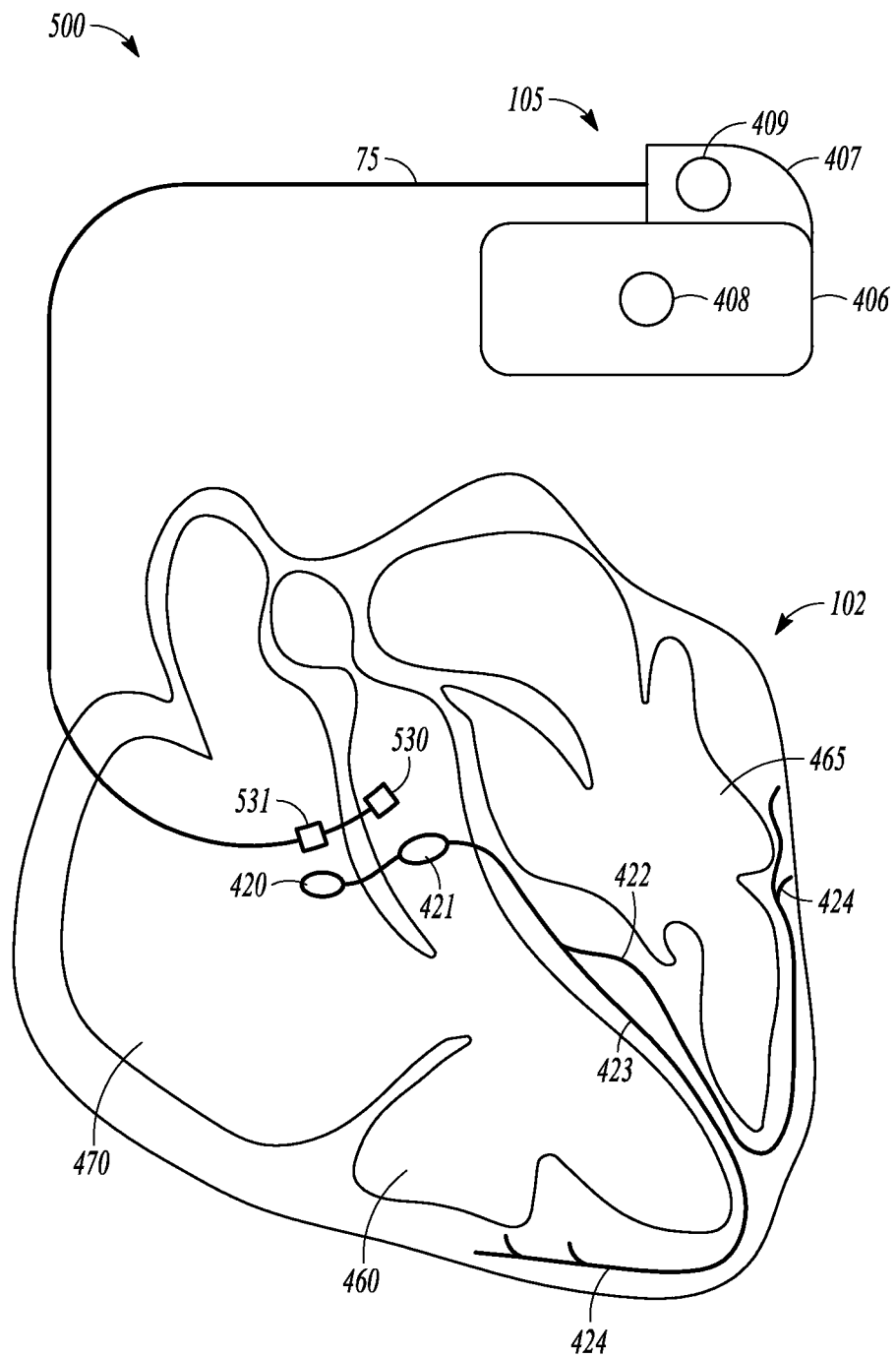
FIG. 5 illustrates generally an example of a system or portion of a system for delivering cardiac therapy or monitoring cardiac activity.

FIG. 5 illustrates generally an atrial lead 75, coupled to a tip electrode 530 and a ring electrode 531. The tip electrode 530 and ring electrode 531 can be disposed in the right atrium near the His-bundle 421 and configured to deliver stimulation energy to the His-bundle 421. In an example, the atrial lead 75 can be used as a sensor, such as to provide information about a physical displacement of at least a portion of the atrial lead 75 in a body. For example, the atrial lead 75 can be electrically coupled to an excitation circuit and a detection circuit, such as can be included in the IMD 105. The excitation circuit can be configured to provide a first signal to the atrial lead 75, and the detection circuit can be configured to receive and interpret a second signal in response to the first signal, the second signal indicative of a physical displacement of the atrial lead 75, as discussed in Ingle U.S. Patent Application No. 61/359,430 entitled "LEAD MOTION SENSING VIA CABLE MICROPHONICS," which is hereby incorporated by reference in its entirety. An elegant and simple system can thus be deployed to pace a heart via the His-bundle and provide a cardiac diagnostic indication, such as an indication of cardiac capture, using a single lead.

Figure 6:
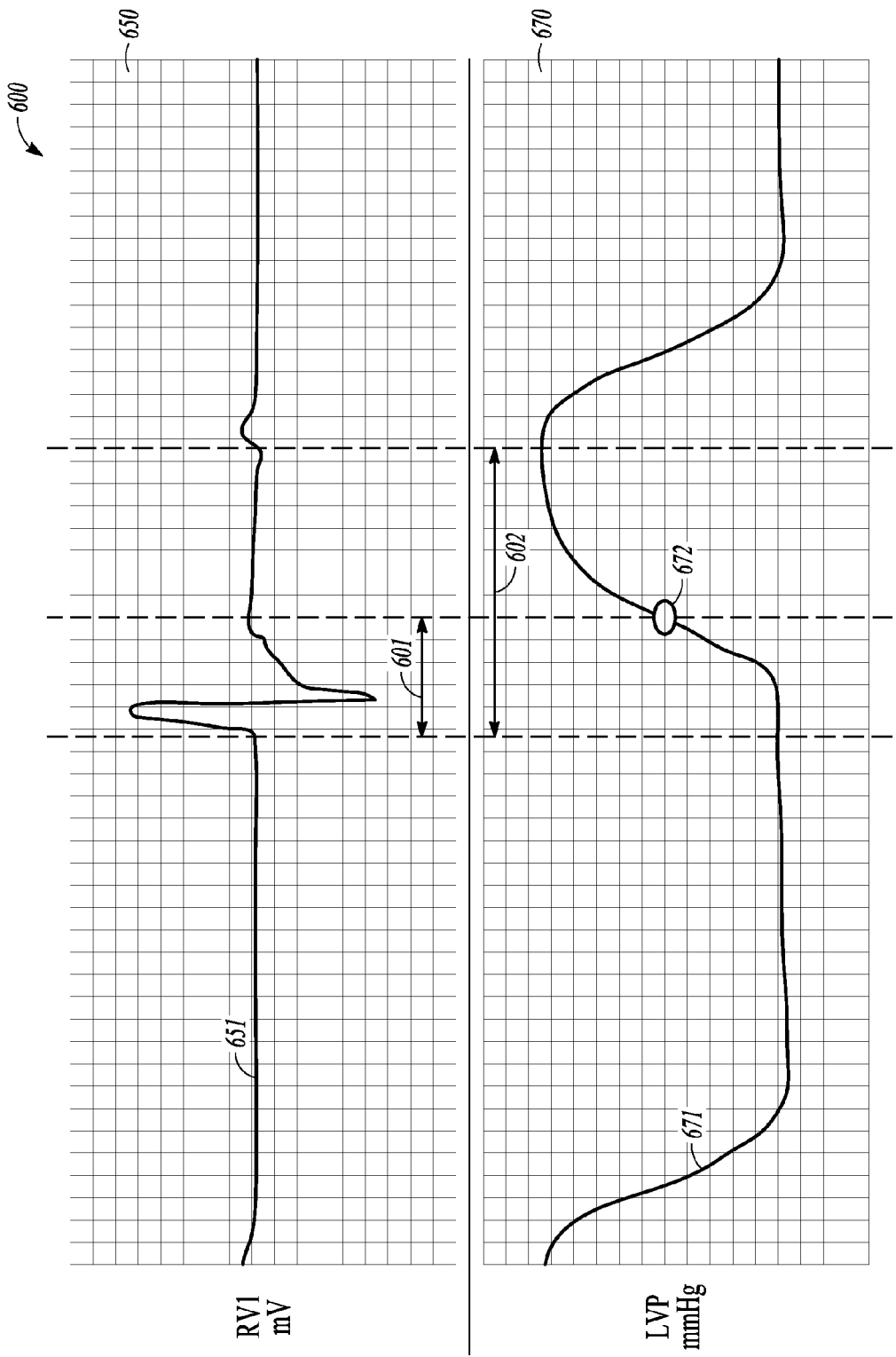
FIG. 6 illustrates generally an example of measuring a time interval using electrical and pressure signals.

FIG. 6 illustrates generally an example of measuring time intervals using cardiac activity information, such as electro-mechanical delay information. The upper chart 650 illustrates generally an example of an electrical signal over time, RV1, such as can be measured using an electrode 66C disposed at or near the His-bundle. In an example, the electrical signal 651 depicted in the upper chart 650 can be indicative of an electrical pacing signal magnitude.

The lower chart 670 illustrates generally a pressure signal over time, LVP, such as a pressure signal indicative of a pressure in the left ventricle. In an example, the lower chart 670 can illustrate a pulmonary artery pressure, or a signal derived from a sensor configured to measure physical displacement or acceleration. The lower chart 670 can provide information about a blood pressure measured using an external arm cuff. The upper chart 650 and lower chart 670 can share a common time axis.

In an example, a time interval, such as can be indicative of electro-mechanical delay in cardiac function, can be measured between a His-bundle pacing marker and a pressure change marker. In an example, a first time interval 601 can be measured between an initial voltage threshold crossing (e.g., 3 mV) of the electrical signal 651 and a point of interest on the lower chart 670, such as a first inflection point 672 on the pressure curve 671. In an example, a second time interval 602 can be calculated between an initial voltage threshold crossing and a maximum pressure change, such as $dP/dt_{max}$. The first time interval 601 or the second time interval 602 can be used as an indication of delay or interval length between a sensed or paced event, such as at the His-bundle 421, and a corresponding physiological response, such as a pressure change in a heart chamber.

Figure 7:
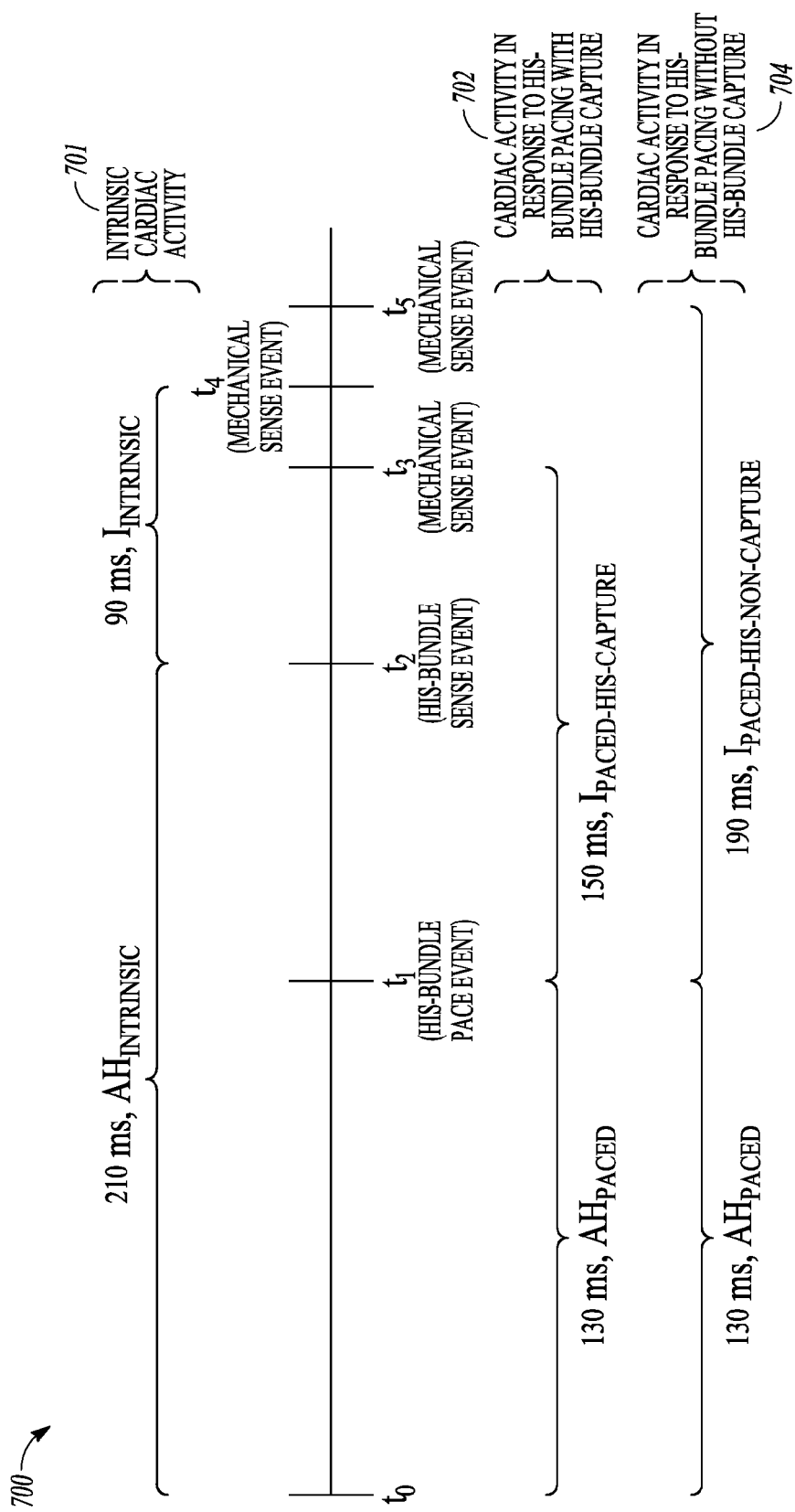
FIG. 7 illustrates generally an example of a timeline illustrating time intervals related to intrinsic cardiac activity and cardiac activity in response to His-bundle stimulation.

FIG. 7 illustrates generally an example of timeline describing pacing and sensing events. Three scenarios are illustrated: intrinsic cardiac activity 701, cardiac activity in response to His-bundle pacing with His-bundle capture 702, and cardiac activity in response to His-bundle pacing without His-bundle capture 704. The AH interval can represent a time interval from a sense or pace event at the atrium to the arrival of an electrical signal at a His-bundle (e.g., from the AV node 420 to the His-bundle 421).

In an example illustrating intrinsic cardiac activity 701, a subject-specific intrinsic AH interval can be 210 ms. In the example of FIG. 7, a 210 ms interval, $AH_{intrinsic}$, is illustrated between $t_0$ and $t_2$. Time $t_2$ can represent an arrival of an electrical signal, a physical atrial activation, a pressure change, or other indication of cardiac activity, such as in response to the arrival of an electrical signal, such as an intrinsic electrical or chemical signal, at the His-bundle 421. In response to intrinsic activation of the AV node, an intrinsic delay interval can be measured as the interval from the end of the $AH_{intrinsic}$ interval (e.g., from time $t_2$) to, for example, a pressure rise marker (e.g., $dP/dt_{max}$) indicative of a cardiac contraction. In the example of FIG. 7, time $t_4$ corresponds to a mechanical sense event, such as received heart sound information indicative of left ventricular activity. In an example, the mechanical sense event at time $t_4$ corresponds to the intrinsic activation through the AV node. In this example, an intrinsic electrical signal can be sensed in the atrium, such as at the AV node 420, at $t_0$, and the His-bundle 421 is intrinsically activated 210 ms later, at $t_2$. Using the heart's natural conduction mechanisms, an intrinsic interval, $I_{intrinsic}$, follows His-bundle activation. In an example, $I_{intrinsic}$ describes the interval beginning after His-bundle activation, including conduction time of the left branch bundle and the Purkinje fibers, and terminating at a mechanical sense event, such as left ventricular activity, such as can be detected at $t_4$, 90 ms after His-bundle activation.

His-bundle pacing can generally be implemented at an interval that is less than an $AH_{intrinsic}$ interval. In an example illustrating cardiac activity in response to His-bundle pacing with His-bundle capture 702, the His-bundle 421 can be paced at $t_1$, such as after an initial delay of 130 ms (e.g., 80 ms before an expected intrinsic activation of the His-bundle 421 at $t_2$). If His-bundle capture is achieved in response to a His-bundle pace event at $t_1$, a first non-intrinsic interval, such as 150 ms, can follow. For example, the first non-intrinsic interval, $I_{paced-His-capture}$, can indicate an interval from the His-bundle pace event at $t_1$ to receipt of mechanical sense event information at $t_3$, such as accelerometer information indicative of cardiac contraction.

If His-bundle capture is not achieved in response to the pace at $t_1$, a second non-intrinsic interval, greater than 150 ms, can be expected. In an example illustrating cardiac activity in response to His-bundle pacing without His-bundle capture 702, the second non-intrinsic interval, $I_{paced-His-NON-capture}$, can indicate a 190 ms interval from the His-bundle pace event at $t_1$ to receipt of mechanical sense event information at $t_4$. The 190 ms interval, $I_{paced-His-NON-capture}$, can indicate cell-to-cell conduction, or signal propagation via other means less efficient than the His-bundle, left or right branch bundles, and the Purkinje fibers. The 150 ms interval, $I_{paced-His-capture}$, can indicate more efficient cardiac activity in response to Purkinje fiber activation.

In the example of FIG. 7, only one of the mechanical sense events $t_3$, $t_4$, or $t_5$, will occur in the ventricle. For example, either the mechanical sense event at $t_4$ will occur in response to intrinsic cardiac activity, or one of the mechanical sense events at $t_3$ or $t_5$ will occur in response to the His-bundle pace event at $t_1$.

Figure 8:
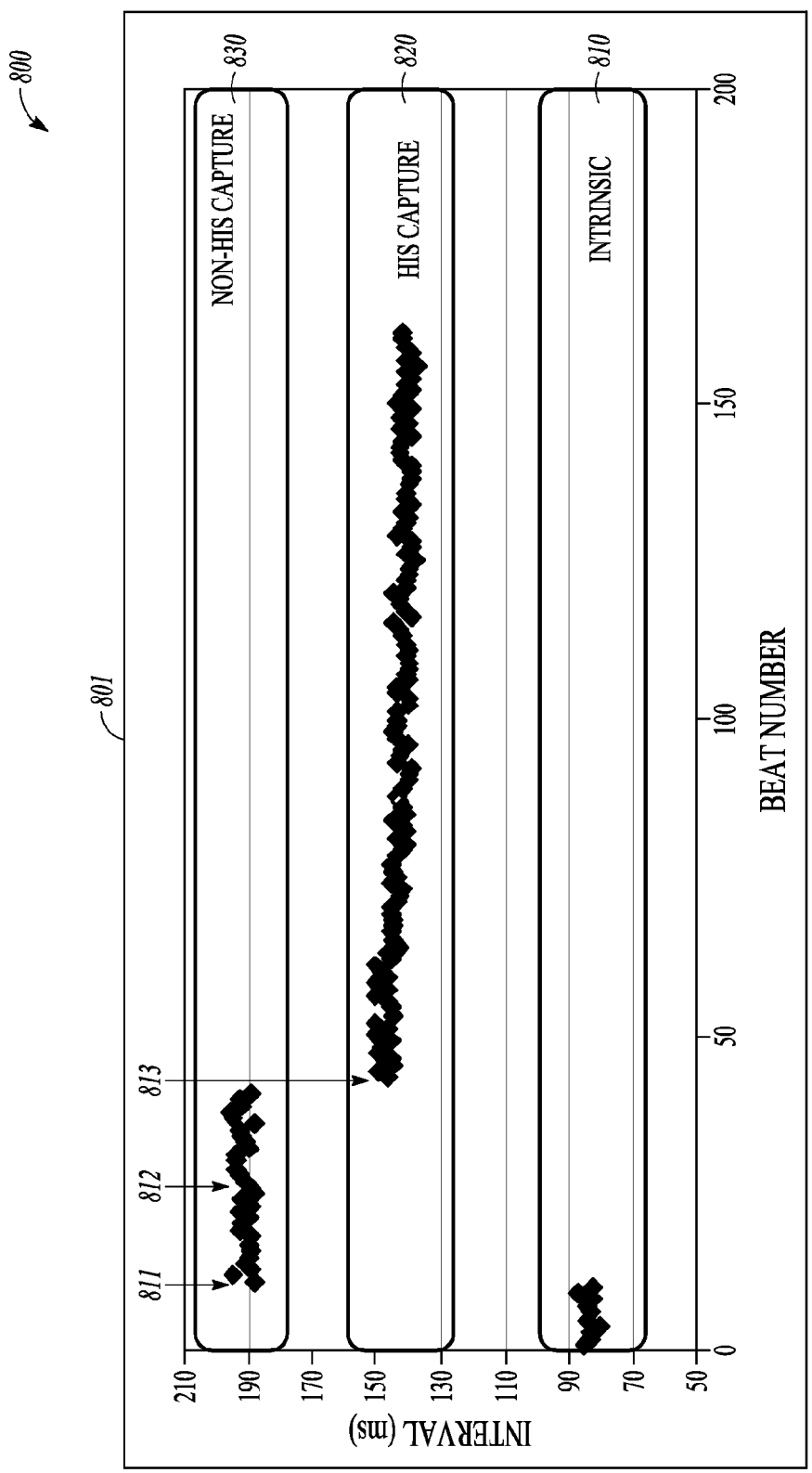
FIG. 8 illustrates generally an example of intervals describing various types of cardiac activity.

FIG. 8 illustrates generally an example of a chart 801 including several intervals describing cardiac function. The x-axis can represent a sequence of cardiac activations, or beats, such as a sequence of one hundred beats. The y-axis can represent a time interval, in milliseconds. In an example, the Intrinsic interval 810 can indicate an interval describing intrinsic cardiac function, such as the interval $I_{intrinsic}$ in FIG. 7. In the example of FIG. 8, the Intrinsic interval 810 includes approximately $I_{intrinsic}$=68 ms to 105 ms. In the example of FIG. 7, $I_{intrinsic}$ can be 90 ms, such as to describe a time interval from a first sense event (e.g., His-bundle activation) to a second sense event (e.g., $dP/dt_{max}$). Thus, in the example of FIG. 8, $I_{intrinsic}$ can be plotted in Intrinsic interval 810. The ten beats in the intrinsic Interval 810 can represent natural cardiac activity, such as without a pacing influence.

After the first ten intrinsic beats, pacing at the His-bundle 421 can begin, such as at 811 using the sixth electrode 66C. In an example, pacing can begin at 0.5V and increase in magnitude until His-bundle activation is achieved. In an example, His-bundle activation can be monitored via a 12-lead ECG array, such as during an IMD implantation procedure. The Non-His-capture interval 830, such as from approximately 178 ms to 208 ms, can indicate an interval describing either the intrinsic activation from the time of His-bundle pacing, or non-intrinsic cardiac function without activation of the His-bundle 421. Such non-intrinsic cardiac function can include cell-to-cell conduction of a pacing stimulus, among other mechanisms. The Non-His-capture interval is expected to be a long duration because the cardiac activity is not activated, at least in part, via the efficient natural conduction mechanisms such as the Purkinje fibers, or left or right branch bundles. In the example of FIG. 7, the interval from a His-bundle pace event at $t_1$ to a mechanical sense event (e.g., an acceleration measured using an accelerometer) at $t_5$, $I_{paced-His-NON-capture}$, can be 190 ms, indicative of non-capture of the His-bundle.

In the example of FIG. 8, the magnitude of a His-bundle pacing stimulation energy can be increased, such as in 0.5V increments after every ten beats, until successful His-bundle pacing is observed. Thus, at 811 the magnitude of the pace signal can be 0.5V, at 812 the magnitude can be 1.0V, and at 813 the magnitude can be 1.5V. At 813, with a His-bundle pacing stimulation energy of 1.5V, His-bundle activation can be achieved. The magnitude of the required His-bundle pacing stimulation energy can depend on a subject's physiology, and the placement of an electrode configured to deliver the His-bundle pacing stimulating energy. His-bundle activation may be achieved with a greater or lesser signal magnitude, and would have to be determined via appropriate experimentation. In the example of FIG. 8, 1.5V is sufficient to activate the His-bundle.

An indication that the His-bundle has been activated can be a decrease in the interval from a His-bundle pace event (e.g., $t_1$ in FIG. 7) to a mechanical sense event detecting a response to the His-bundle pace event. In an example, the data point at 813 can represent the interval $I_{paced-His-capture}$. In an example, the sense event can include the detection of a heart sound signal indicative of physical cardiac activity, such as a heart valve opening or closing. The 150 ms interval $I_{paced-His-capture}$ can be plotted on the chart 801 in the His-capture interval 820.

FIG. 8 illustrates the distinct intervals including the Intrinsic interval 810, the His-capture interval 820, and the Non-His-capture interval 830. In an example, intrinsic cardiac activity 701 can be included in the Intrinsic interval 810, cardiac activity in response to His-bundle pacing with His-bundle capture 702 can be included in the His-capture interval 820, and cardiac activity in response to His-bundle pacing without His-bundle capture 704 can be included in the Non-His capture interval 830.

In the example of FIG. 8, a cardiac diagnostic indication can be provided using the intervals 810, 820, and 830, or similar intervals derived for a particular subject. The cardiac diagnostic indication can include information about whether or not a His-bundle pace event has successfully activated the His-bundle 421. In an example, the cardiac diagnostic indication can be used to classify cardiac activity as intrinsic activity, non-intrinsic activity due to His-bundle activation, and non-intrinsic activity not due to His-bundle activation. For example, an intrinsic interval can be determined, using a subject's $I_{intrinsic}$. In an example, a test interval can be measured beginning at a His-bundle pacing stimulation energy application time (e.g., $t_1$ in FIG. 7), and ending with the detection of mechanical cardiac activity (e.g., $t_3$ or $t_5$ in FIG. 7). The test interval can be compared to a subject's $I_{intrinsic}$, or compared to other test intervals. For example, other test intervals can include intervals describing responses to several His-bundle pacing stimulation energies.

Figure 9:
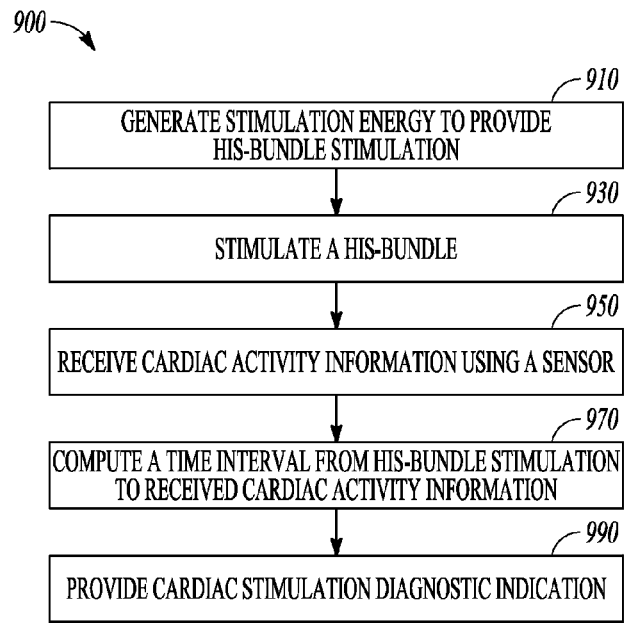
FIG. 9 illustrates generally an example that can include generating stimulation energy, stimulating a His-bundle, receiving cardiac activity information using a sensor, computing a time interval, and providing a cardiac stimulation diagnostic indication.

FIG. 9 illustrates generally an example 900 that can include generating stimulation energy to provide His-bundle stimulation 910, stimulating a His-bundle 930, receiving cardiac activity information using a sensor 950, computing a time interval from His-bundle stimulation to received cardiac activity information 970, and providing a cardiac stimulation diagnostic indication 990. In an example, the example 900, or any prior or subsequent examples presented herein, can be implemented in an IMD programmer device, such as during an IMD implantation procedure. In an example, the example 900, or any prior or subsequent examples presented herein, can be implemented in an IMD and can be adjusted, such as using the external module 115 for periodic testing or patient follow-up.

At 910, a stimulation energy can be generated, such as to provide a pacing signal to the His-bundle 421. In an example, the stimulation energy can be generated using the cardiac stimulation circuit 110 in the IMD 105. In an example, the pulse generator 350 can be configured to provide the stimulation energy, such as including a biphasic stimulation energy signal.

At 930, the stimulation energy can be provided to the His-bundle 421, such as via the electrode 360, or the tip electrode 530, among other electrodes or electrode combinations, disposed in or about the His-bundle. An electrophysiological mapping can be performed to locate the intracardiac region wherein the stimulation energy can be delivered to the His-bundle most efficiently. Among other techniques, an appropriate intracardiac region can be located using the systems and methods described by Liu et al., U.S. Pat. No. 7,245,973 entitled "HIS BUNDLE MAPPING, PACING, AND INJECTION LEAD," which is hereby incorporated by reference in its entirety.

At 950, cardiac activity information can be received. In an example, the cardiac activity information can include electrical or mechanical information about a physical displacement of cardiac tissue or a blood flow condition inside the heart. For example, cardiac activity information can include information, such as time information, regarding a particular mechanical motion, such as a contraction. Other mechanical motions can include a contraction or relaxation of a particular ventricle or atrium, an opening or closing of a heart valve, or a physical location change of a portion of cardiac tissue, among others. Cardiac activity information can include electrical information, such as a change in impedance or a change in an electric field. Cardiac activity information can include blood flow rate information, or pressure information, such as information about a central venous pressure at a first time, a left ventricular pressure at a second time, or a pulmonary artery pressure at a third time, among others. Cardiac activity information can include electrical signal information, such as electrical signal information sensed using an electrode disposed in a ventricle. For example, cardiac activity information can include electrical signal information obtained using an electrode disposed in the right ventricle near the apex, or disposed in the left ventricular free wall.

Cardiac activity information can be received at 950 via sensors configured to detect electrical or mechanical activity associated with cardiac function. In an example, the sensors can be configured to provide information to the cardiac sensing circuit 111. For example, a sensor can include an electrode configured to measure an impedance signal, such as an intracardiac impedance signal. A sensor can include a plurality of electrodes configured to measure an electric field. In an example, the plurality of electrodes can be coupled to the processor circuit 112, such as to monitor an electric field over time to determine a mechanical activity of the heart.

A sensor configured to provide cardiac activity information can include a pressure sensor. For example, a pressure sensor can be disposed in the thoracic vena cava of a subject to provide a central venous pressure. Cardiac activity information, such as the portion of the cardiac cycle, can be determined using pressure change information, such as central venous pressure change information collected over time, such as using the processor circuit 112. Other pressure sensors can be used to provide cardiac activity information, such as an external blood pressure cuff, or a Finapres device, among others.

A sensor configured to provide cardiac activity information can include an accelerometer. In an example, an accelerometer can be configured to provide activity level information about a subject. An accelerometer positioned in or near cardiac tissue can provide information about cardiac tissue displacement, such as to indicate heart sound information, such as S1 or S2.

At 970, a time interval can be computed. In an example, cardiac activity information can include timing information. Cardiac activity information can include time interval measurements, such as an interval from an observed intrinsic His-bundle activation to an observed intrinsic cardiac response. In an example, an electrode disposed in or near the His-bundle can detect intrinsic His-bundle activation at time $t_2$ (see FIG. 7). Cardiac activity information can include information such as the length of the interval between $t_2$ and the detection of mechanical cardiac activity, such as via a central venous pressure sensor. In an example, cardiac activity information can include information such as the length of the interval between $t_2$ and the detection of electrical activity indicative of cardiac tissue displacement, such as an impedance measurement provided via an electrode disposed in or near the right or left ventricle. In an example, cardiac activity information can include stroke volume timing information over time, such as a time-dependent stroke volume signal, such as can be provided via an intracardiac or intrathoracic impedance measurement.

In an example, cardiac activity information can include time interval measurements, such as an interval from a His-bundle pace event to an observed cardiac response. In an example, an electrode disposed in or near the His-bundle can stimulate the His-bundle at time $t_1$ (see FIG. 7). Cardiac activity information can include information such as the length of the interval between $t_1$ and detected mechanical cardiac activity. In an example, mechanical cardiac activity in response to a His-bundle pace event can be detected using any of the sensors or methods described herein.

At 990, a cardiac stimulation diagnostic indication can be provided. As described above in the discussion of FIG. 7, the length of the interval between $t_1$ and detected mechanical cardiac activity can depend on whether the His-bundle was successfully paced at $t_1$. In an example, a successful His-bundle pace can result in a first duration. An unsuccessful His-bundle pace can result in a second duration, which is generally expected to be longer than the first duration.

In an example, multiple durations, intervals, ranges, can be determined for successful His-bundle paces, unsuccessful His-bundle paces, and intrinsic cardiac activity. An example of such ranges is show in FIG. 8. These ranges can be used to form a cardiac stimulation diagnostic or comparison metric, and can be used on a forward-basis to assess or diagnose later cardiac activity. For example, the cardiac stimulation diagnostic metric can be used to classify cardiac activity information as cardiac function via intrinsic conduction, cardiac function via successful His-bundle activation, or cardiac function after unsuccessful His-bundle activation.

Figure 10:
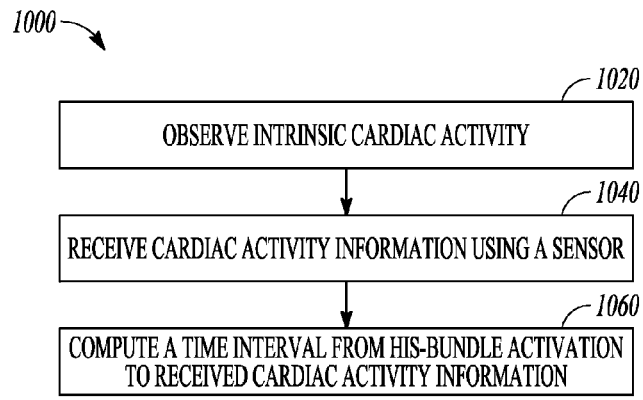
FIG. 10 illustrates generally an example that can include observing intrinsic cardiac activity, receiving cardiac activity information, and computing a time interval.

FIG. 10 illustrates generally an example 1000 that can include observing intrinsic cardiac activity 1020, receiving cardiac activity information 1040, and computing a time interval from His-bundle activation to received cardiac activity information 1060. In an example, the example 1000 can be combined with the example 900.

At 1020, intrinsic cardiac activity can be observed. As discussed at length above, such as in the discussions of FIG. 7 and FIG. 10, intrinsic cardiac activity can include intrinsic activation of the His-bundle, or receipt of an intrinsic electrical or chemical signal at one or more of the SA or AV nodes. Intrinsic cardiac activity can include other mechanical or electrical activity associated with unaided cardiac function. For example, intrinsic cardiac activity can include cardiac contractions in response to Purkinje fiber conduction of intrinsic signals. For purposes of computing or observing a time interval variable, intrinsic cardiac activity can be observed at a first time, such as time $t_2$ in FIG. 7.

At 1040, cardiac activity information can be received, such as using a sensor. The receipt of cardiac activity information can be achieved such as according to the discussion of FIG. 9 at 950. In an example, the cardiac activity information can be indicative of a cardiac activity response to an intrinsic cardiac signal.

At 1060, a time interval can be calculated, such as the time interval from intrinsic His-bundle activation to received cardiac activity information (e.g., $I_{intrinsic}$ in FIG. 7). In an example, a time interval representative of intrinsic cardiac activity can be plotted, such as using the chart 801. The time interval representative of intrinsic activity can be used to establish a first range of time intervals, such as can be indicative cardiac function in response to intrinsic signals. Generally, this range can be expected to be of a minimum duration because the natural and most efficient conduction mechanisms of the heart are used.

Figure 11:
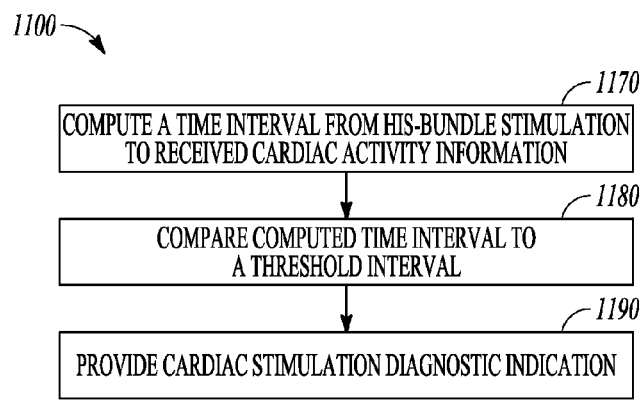
FIG. 11 illustrates generally an example that can include computing a time interval, comparing an interval to a threshold, and providing a cardiac stimulation diagnostic indication.

FIG. 11 illustrates generally an example 1100 that can include computing a time interval 1170, comparing the time interval to a threshold interval 1180, and providing a cardiac stimulation diagnostic indication 1190.

At 1170, a time interval can be computed, such as from a His-bundle stimulation time to a time indicative of cardiac activity information. In an example, the time interval can include intrinsic cardiac activity information, or cardiac activity information received in response to pacing the His-bundle 421, such as using the cardiac stimulating circuit 110. In an example, the time interval can be computed according to the discussion of FIG. 9 at 970.

At 1180, the computed time interval can be compared to a threshold value, or to a set of values. For example, an electrophysiologist can establish a range of intervals expected for conduction of intrinsic cardiac signals in a particular patient. In an example, intrinsic cardiac signals can have intervals of approximately 68 ms to 95 ms, or 81.5+/−13.5 ms.

In an illustrative example, the computed time interval can be 80 ms, and the threshold value can be 95 ms. At 1180, the time interval 80 ms can be compared to the threshold value 95 ms. In an example, the processor circuit 112 can execute instructions, such as can be received from the processor-readable medium 320, to provide a cardiac stimulation diagnostic indication at 1190. For example, the time interval 80 ms can be classified using the processor circuit 112 as an intrinsic cardiac signal because it falls below the threshold value of 95 ms. This classification can be stored, shared with other devices or IMD 105 components, analyzed for an indication of therapy, or communicated to the external module 115, among others.

In a second illustrative example, the computed time interval can be 150 ms. Comparison of the computed time interval with a threshold interval at 1180 can, for example, indicate that the 150 ms interval is not indicative of intrinsic cardiac activity. Further processing, such as using the processor circuit 112 and further comparisons with stored values, such as threshold values, the 150 ms time interval can be classified as indicative of cardiac capture. See FIG. 7 at 702, and FIG. 8 at 820.

Figure 12:
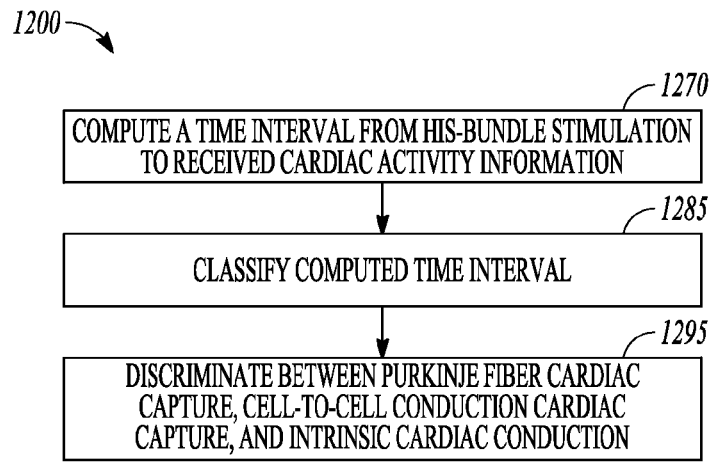
FIG. 12 illustrates generally an example that can include computing a time interval, classifying a time interval, and discriminating between Purkinje fiber cardiac capture, cell-to-cell cardiac capture, and intrinsic cardiac conduction.

FIG. 12 illustrates generally an example 1200 that can include computing a time interval from His-bundle stimulation to received cardiac activity information 1270, classifying a computed time interval 1285, and discriminating between Purkinje fiber cardiac capture, cell-to-cell conduction cardiac capture, and intrinsic cardiac conduction 1295.

At 1270, a time interval can be computed, such as from a His-bundle stimulation time to a time indicative of cardiac activity information. In an example, the time interval can include intrinsic cardiac activity information, or cardiac activity information received in response to pacing the His-bundle 421, such as using the cardiac stimulating circuit 110. In an example, the time interval can be computed according to the discussion of FIG. 9 at 970.

At 1285, a time interval, such as the time interval computed at 1270, can be classified. In an example, the time interval can be compared to a threshold, such as according to the discussion of FIG. 11 at 1180, and classified using a result of the comparison. In an example, the classification can be accomplished using the processor circuit 112. In an example, the classification can be accomplished using the time interval as an input to a subject-specific function that can provide discrimination among various types of cardiac activity.

For example, at 1295, the time interval can be used to discriminate between Purkinje fiber cardiac capture, and cardiac capture via cell-to-cell conduction. In response to a successful His-bundle pace event, the Purkinje fibers will be activated via their natural and most efficient means, resulting in a coordinated mechanical cardiac response. In contrast, an unsuccessful His-bundle pace event may trigger cardiac capture via cell-to-cell conduction, such as conduction using myocardial tissue. Although both scenarios may result in contraction of cardiac tissue, the time interval between the pace event and a sensed mechanical response to the pace event can differ. Thus, in an example, a small interval can indicate Purkinje fiber cardiac capture, such as can be discriminated from cardiac capture via cell-to-cell conduction. An even smaller duration interval can indicate cardiac contraction in response to intrinsic cardiac conduction (e.g., an intrinsic signal is present at the AV node, which activates the His-bundle and Purkinje fibers to naturally coordinate the cardiac activity).

In an example, the discrimination at 1295 can include the provision of a cardiac stimulation diagnostic indication, such as described at length in FIG. 9 at 990 and FIG. 11 at 1190.

Figure 13:
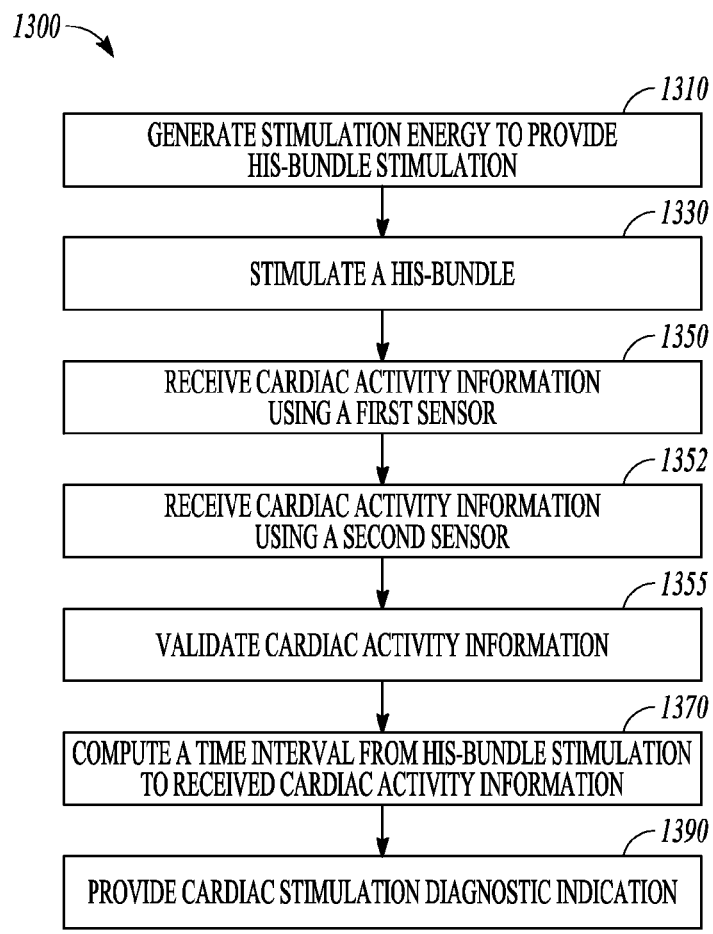
FIG. 13 illustrates generally an example that can include generating a stimulation energy, stimulating a His-bundle, receiving cardiac activity information from more than one source, validating cardiac activity information, computing a time interval, and providing a cardiac stimulation diagnostic indication.

FIG. 13 illustrates generally an example 1300 that can include generating stimulation energy 1310, stimulating a His-bundle 1330, receiving cardiac activity information using a first sensor 1350, receiving cardiac activity information using a second sensor 1352, validating cardiac activity information 1355, computing a time interval 1370, and providing a cardiac stimulation diagnostic indication 1390.

At 1310, a stimulation energy can be generated to provide His-bundle stimulation, such as according to the discussion of FIG. 9 at 910. At 1330, a His-bundle can be stimulated, such as according to the discussion of FIG. 9 at 930.

At 1350, cardiac activity information can be received using a first sensor. In an example, the cardiac activity information can be received according to any of the methods or systems described in FIG. 9 at 950. For example, a pace event trigger can be received using an electrode. In an example, S1 heart sound information can be received using an accelerometer.

At 1352, cardiac activity information can be received using a second sensor. In an example, the cardiac activity information can be received according to any of the methods or systems described in FIG. 9 at 950. In an example, the second sensor is the same as the first sensor, but the second sensor is configured to provide cardiac activity information at a different time than the first sensor. For example, the first sensor can be an accelerometer configured to detect S1 heart sounds. The second sensor can be the same accelerometer but configured to detect S2 heart sounds.

In an example, the second sensor can be a different sensor than the first sensor. For example, the first sensor can be a pressure sensor disposed in the thoracic vena cava, and configured to measure changes in central venous pressure over time. The second sensor can be an accelerometer configured to detect left ventricular movement. In an example, a plurality of additional sensors can be disposed in or near the heart 102 and configured to provide cardiac activity information.

At 1355, cardiac activity information can be validated using the cardiac activity information received from the first and second sensors. Because one or both of the sensors can be subject to noise, validation of a signal indicative of cardiac activity can be an important step to avoid an indication of therapy where it is not warranted.

In an example, the first and second sensors can be the same sensor configured to receive information at different times. For example, the first sensor can be configured to detect an S1 heart sound and the second sensor can be configured to detect an S2 heart sound. Heart sound detectors, such as accelerometers, can be prone to interference such as noise due to patient movement, respiration, or other artifacts.

In an example, information received using the first sensor can indicate an Si heart sound when in fact the signal is noise. The second sensor can augment, or validate, the heart sound information. For example, an S1 heart sound is generally expected to be a "lub" sound with a particular frequency content. The S2 heart sound is generally expected to be a "dub" sound with a frequency content different than the S1 sound. If both the S1 and S2 heart sounds are not detected, such as within a particular time window using the first sensor and the second sensor, any S1-like sound detected using the first sensor can be dismissed as noise.

In an example, the first and second sensors can be different sensors, such as can be configured to receive information concurrently, sequentially, or during overlapping periods. For example, the first sensor can be an accelerometer configured to detect left ventricular motion. The second sensor can be a pressure sensor disposed in the thoracic vena cava near the right atrium. In an example, cardiac activity information received from the first sensor can be indicative of left ventricular contraction, but the second sensor may not indicate an expected pressure change, such as within a particular time window. In such an example, the cardiac activity information from the first sensor can be discarded, or the system 100 can be configured to augment the cardiac activity information using other means, such as using additional sensors or further processing the first sensor signal.

At 1370, a time interval can be computed, such as according to the discussion of FIG. 9 at 970. At 1390, a cardiac stimulation diagnostic indication can be provided, such as according to the discussion of FIG. 9 at 990.

ADDITIONAL NOTES & EXAMPLES

Example 1 includes subject matter, such as an ambulatory medical device, comprising a cardiac stimulation circuit configured to generate a stimulation energy to provide His-bundle stimulation. Example 1 can include a processor circuit, including a data input, configured to receive first cardiac activity information, from other than an intrinsic electrical heart signal, such as using a first sensor. Example 1 can include subject matter such as a processor-readable medium, including instructions that, when performed by the processor, configure the medical device to determine a first interval using the first cardiac activity information, and provide a cardiac stimulation diagnostic indication using the first interval.

In Example 2, the subject matter of Example 1 can optionally include a processor circuit, including a data input configured to receive intrinsic cardiac activity information using the first sensor.

In Example 3, the subject matter of one or any combination of Examples 1-2 can optionally include a processor-readable medium including instructions that, when performed by the processor, configure the medical device to provide the cardiac stimulation diagnostic indication using the first interval and the intrinsic cardiac activity information.

In Example 4, the subject matter of one or any combination of Examples 1-3 can optionally include a processor-readable medium including instructions that, when performed by the processor, configure the medical device to discriminate between Purkinje fiber cardiac capture, cell-to-cell conduction cardiac capture, and intrinsic conduction cardiac contraction.

In Example 5, the subject matter of one or any combination of Examples 1-4 can optionally include a processor circuit, including a data input configured to receive first cardiac activity information from an indication of central venous pressure, such as from a pressure sensor disposed in a vein.

In Example 6, the subject matter of one or any combination of Examples 1-5 can optionally include a processor circuit, including a data input configured to receive first cardiac activity information from an intracardiac or thoracic impedance, such as can be provided by an electrode configured to measure impedance.

In Example 7, the subject matter of one or any combination of Examples 1-6 can optionally include a processor-readable medium including instructions that, when performed by the processor, configure the medical device to provide a cardiac stimulation diagnostic indication using a stroke volume signal measured using an electrode.

In Example 8, the subject matter of one or any combination of Examples 1-7 can optionally include a processor circuit, including a data input configured to receive first cardiac activity information from an indication of a heart sound, such as can be provided by an accelerometer.

In Example 9, the subject matter of one or any combination of Examples 1-8 can optionally include a processor circuit, including a second data input configured to receive second cardiac activity information using a second sensor that can be different than the first sensor. In an example, the second cardiac activity information can be used to augment the first cardiac activity information.

Example 10 can include, or can be combined with the subject matter of one or any combination of Examples 1-9 to optionally include subject matter such as an ambulatory medical device, comprising a cardiac stimulation circuit configured to generate a stimulation energy to provide His-bundle stimulation, and a processor circuit, including a first data input, configured to receive first cardiac activity information, from an intrinsic electrical heart signal, using a first sensor, and a second data input, configured to receive second cardiac activity information, from other than an intrinsic electrical heart signal, using the first sensor. Example 10 can include a processor-readable medium, including instructions that, when performed by the processor, configure the medical device to determine a first interval using the first cardiac activity information, determine a second interval using the second cardiac activity information, form a cardiac stimulation diagnostic metric using at least the first interval, and provide a cardiac stimulation diagnostic indication using the cardiac stimulation diagnostic metric and the second interval.

In Example 11, the subject matter of one or any combination of Examples 1-10 can optionally include subject matter (such as a method, a means for performing acts, or a machine-readable medium including instructions that, when performed by the machine, cause the machine to perform acts) that can include generating, using an ambulatory medical device, a stimulation energy to provide His-bundle stimulation, stimulating a His-bundle at a first time using the stimulation energy, receiving first cardiac activity information, from other than an intrinsic electrical heart signal, from a first sensor at a second time, wherein the first cardiac activity information can be indicative of a cardiac response to the stimulating. Example 11 can include computing a first time interval using the first time and the second time, and providing a cardiac stimulation diagnostic indication using the computed first time interval.

In Example 12, the subject matter of one or any combination of Examples 1-11 can optionally include providing a cardiac stimulation diagnostic indication, such as by comparing the first time interval to a threshold interval.

In Example 13, the subject matter of one or any combination of Examples 1-12 can optionally include observing an intrinsic His-bundle activation at a third time, receiving intrinsic cardiac activity information from the sensor at a fourth time, the intrinsic cardiac activity information indicative of a cardiac response to the intrinsic His-bundle activation, and computing the threshold interval using the third time and the fourth time.

In Example 14, the subject matter of one or any combination of Examples 1-13 can optionally include providing a cardiac stimulation diagnostic indication, such as discriminating between Purkinje fiber cardiac capture, cell-to-cell conduction cardiac capture, and intrinsic conduction cardiac contraction.

In Example 15, the subject matter of one or any combination of Examples 1-14 can optionally include receiving first cardiac activity information from a first sensor, such as receiving cardiac activity information from an indication of central venous pressure from a pressure sensor.

In Example 16, the subject matter of one or any combination of Examples 1-15 can optionally include receiving first cardiac activity information from a first sensor, such as receiving cardiac activity information from an intracardiac or thoracic impedance provided by an electrode configured to measure impedance.

In Example 17, the subject matter of one or any combination of Examples 1-16 can optionally include receiving first cardiac activity information from a first sensor, such as receiving mechanical cardiac activity information using a lead configured to deliver a stimulating energy.

In Example 18, the subject matter of one or any combination of Examples 1-17 can optionally include receiving first cardiac activity information from a first sensor, such as receiving cardiac activity information from an indication of a heart sound provided by an accelerometer.

In Example 19, the subject matter of one or any combination of Examples 1-18 can optionally include receiving first cardiac activity information from a first sensor, such as receiving cardiac activity information from an indication of QRS axis deviation provided by an array of electrodes disposed on or in a body.

In Example 20, the subject matter of one or any combination of Examples 1-19 can optionally include receiving second cardiac activity information, from other than an intrinsic electrical heart signal, from a second sensor at a third time. The second cardiac activity information can be used to augment first cardiac activity information.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An ambulatory medical device, comprising:
a cardiac stimulation circuit configured to generate a His-bundle stimulation energy to provide stimulation to a His-bundle;
a processor circuit, including:
a data input, configured to receive first cardiac activity information in response to a His-bundle stimulation energy provided by the cardiac stimulation circuit to the His-bundle, the first cardiac activity information from other than an intrinsic electrical heart signal, and the first cardiac activity information received using a first sensor; and
a processor-readable medium, including instructions that, when performed by the processor, configure the medical device to:
determine a first interval using the first cardiac activity information in response to the His-bundle stimulation energy provided by the cardiac stimulation circuit to the His-bundle; and
provide a cardiac stimulation diagnostic indication about His-bundle capture using the first interval.

2. The ambulatory medical device of claim 1, wherein the data input is configured to receive intrinsic cardiac activity information using the first sensor.

3. The ambulatory medical device of claim 2, wherein the processor-readable medium includes instructions that, when performed by the processor, configure the medical device to provide the cardiac stimulation diagnostic indication using the first interval and the intrinsic cardiac activity information.

4. The ambulatory medical device of claim 3, wherein the processor-readable medium includes instructions that, when performed by the processor, configure the medical device to discriminate between Purkinje fiber cardiac capture, cell-to-cell conduction cardiac capture, and intrinsic conduction cardiac capture.

5. The ambulatory medical device of claim 1, wherein the data input is configured to receive first cardiac activity information from an indication of central venous pressure from a pressure sensor.

6. The ambulatory medical device of claim 1, wherein the data input is configured to receive first cardiac activity information from an intracardiac or thoracic impedance provided by an electrode configured to measure impedance.

7. The ambulatory medical device of claim 6, wherein the processor-readable medium includes instructions that, when performed by the processor, configure the medical device to provide the cardiac stimulation diagnostic indication using a stroke volume signal measured using the electrode.

8. The ambulatory medical device of claim 1, wherein the data input is configured to receive first cardiac activity information from an indication of a heart sound provided by an accelerometer.

9. The ambulatory medical device of claim 1, wherein the processor circuit includes a second data input, configured to receive second cardiac activity information using a second sensor different than the first sensor, the second cardiac activity information used to augment the first cardiac activity information.

10. An ambulatory medical device, comprising:
a cardiac stimulation circuit configured to generate a His-bundle stimulation energy to provide stimulation to a His-bundle;
a processor circuit, including:
a first data input, configured to receive first cardiac activity information, from an intrinsic electrical heart signal, using a first sensor; and
a second data input, configured to receive second cardiac activity information in response to a His-bundle stimulation energy provided by the cardiac stimulation circuit to the His-bundle, the second cardiac activity information from other than an intrinsic electrical heart signal, and the second cardiac activity information received using the first sensor; and
a processor-readable medium, including instructions that, when performed by the processor, configure the medical device to:
determine a first interval using the first cardiac activity information;
determine a second interval using the second cardiac activity information in response to the His-bundle stimulation energy provided by the cardiac stimulation circuit to the His-bundle;
form a cardiac stimulation diagnostic metric using at least the first interval; and
provide a cardiac stimulation diagnostic indication about His-bundle capture using the cardiac stimulation diagnostic metric and the second interval.

11. A method comprising:
generating, using an ambulatory medical device, a His-bundle stimulation energy to provide stimulation to a His-bundle;

stimulating a His-bundle at a first time using the His-bundle stimulation energy;
receiving first cardiac activity information, from other than an intrinsic electrical heart signal, from a first sensor at a second time, the first cardiac activity information indicative of a cardiac response to the stimulating the His-bundle at the first time using the His-bundle stimulation energy;
computing a first time interval using the first time and the second time; and
providing a cardiac stimulation diagnostic indication about His-bundle capture using the computed first time interval.

12. The method of claim 11, wherein the providing a cardiac stimulation diagnostic indication includes comparing the first time interval to a threshold interval.

13. The method of claim 12, including:
observing an intrinsic His-bundle activation at a third time;
receiving intrinsic cardiac activity information from the sensor at a fourth time, the intrinsic cardiac activity information indicative of a cardiac response to the intrinsic His-bundle activation; and
computing the threshold interval using the third time and the fourth time.

14. The method of claim 11, wherein the providing a cardiac stimulation diagnostic indication includes discriminating between Purkinje fiber cardiac capture, cell-to-cell conduction cardiac capture, and intrinsic conduction cardiac contraction.

15. The method of claim 11, wherein the receiving first cardiac activity information from a first sensor includes receiving cardiac activity information from an indication of central venous pressure from a pressure sensor.

16. The method of claim 11, wherein the receiving first cardiac activity information from a first sensor includes receiving cardiac activity information from an intracardiac or thoracic impedance provided by an electrode configured to measure impedance.

17. The method of claim 11, wherein the receiving first cardiac activity information from a first sensor includes receiving mechanical cardiac activity information using a lead configured to deliver the stimulating energy.

18. The method of claim 11, wherein the receiving first cardiac activity information from a first sensor includes receiving cardiac activity information from an indication of a heart sound provided by an accelerometer.

19. The method of claim 11, wherein the receiving first cardiac activity information from a first sensor includes receiving cardiac activity information from an indication of QRS axis deviation provided by an array of electrodes disposed on or in a body.

20. The method of claim 11, including receiving second cardiac activity information, from other than an intrinsic electrical heart signal, from a second sensor at a third time, the second cardiac activity information used to augment the first cardiac activity information.

* * * * *